US007837680B2

(12) United States Patent  (10) Patent No.: US 7,837,680 B2
Isaacson et al.  (45) Date of Patent: Nov. 23, 2010

(54) TUNED RETURN ELECTRODE WITH MATCHING INDUCTOR

(75) Inventors: James D. Isaacson, Salt Lake City, UT (US); Paul R. Borgmeier, Salt Lake City, UT (US)

(73) Assignee: Megadyne Medical Products, Inc., Draper, UT (US)

(*) Notice: Subject to any disclaimer, the term of this patent is extended or adjusted under 35 U.S.C. 154(b) by 1090 days.

(21) Appl. No.: 11/537,396

(22) Filed: Sep. 29, 2006

(65) Prior Publication Data

US 2007/0049916 A1  Mar. 1, 2007

Related U.S. Application Data

(63) Continuation of application No. 10/719,333, filed on Nov. 21, 2003, now Pat. No. 7,169,145.

(51) Int. Cl.
*A61B 18/04* (2006.01)
(52) U.S. Cl. .......................................... 606/35; 606/32
(58) Field of Classification Search ................. 606/32, 606/35, 39, 152; 128/908
See application file for complete search history.

(56) References Cited

U.S. PATENT DOCUMENTS

| 3,089,496 | A | 5/1963 | Degelman |
| 3,543,760 | A | 12/1970 | Bolduc |
| 3,601,126 | A | 8/1971 | Estes |
| 3,720,209 | A | 3/1973 | Bolduc |
| 3,848,600 | A | 11/1974 | Patrick, Jr. et al. |
| 4,088,133 | A | 5/1978 | Twentier |
| 4,092,985 | A | 6/1978 | Kaufman |
| 4,094,320 | A | 6/1978 | Newton et al. |
| 4,117,846 | A | 10/1978 | Williams |
| 4,166,465 | A | 9/1979 | Esty et al. |

(Continued)

FOREIGN PATENT DOCUMENTS

GB  1 480 736  7/1977

(Continued)

OTHER PUBLICATIONS

Wald, et al., "Accidental Burns Associated With Electrocautery," *JAMA*, Aug. 16, 1978, vol. 217, No. 7, pp. 916-921.

(Continued)

*Primary Examiner*—Roy D Gibson
(74) *Attorney, Agent, or Firm*—Workman Nydegger

(57) ABSTRACT

An electrosurgical return electrode for use in electrosurgery. The return electrode is self-limiting and self-regulating as to current temperature and temperature rise so as to prevent patient trauma. According to one aspect of the invention, an inductor is coupled in series with the electrosurgical return electrode. The inductor is configured to optimize the flow of the electrosurgical current by minimizing the effective bulk impedance of the electrosurgical return electrode when the amount of contact area between the patient and the electrosurgical return electrode is sufficient to conduct electrosurgery. According to another aspect of the present invention, a conductor member is adapted for use with circuitry that indicates to a user when the contact area between the patient and the self-limiting member and/or return electrode is below a given threshold.

21 Claims, 13 Drawing Sheets

U.S. PATENT DOCUMENTS

| | | |
|---|---|---|
| 4,188,927 A | 2/1980 | Harris |
| 4,200,104 A | 4/1980 | Harris |
| 4,207,904 A | 6/1980 | Greene |
| 4,226,247 A | 10/1980 | Hauser et al. |
| 4,231,372 A | 11/1980 | Newton |
| 4,237,886 A | 12/1980 | Sakurada et al. |
| 4,237,887 A | 12/1980 | Gonser |
| 4,267,840 A | 5/1981 | Lazar et al. |
| 4,304,235 A | 12/1981 | Kaufman |
| 4,384,582 A | 5/1983 | Watt |
| 4,387,714 A | 6/1983 | Geddes et al. |
| 4,669,468 A | 6/1987 | Cartmell et al. |
| 4,770,173 A | 9/1988 | Feucht et al. |
| 4,799,480 A | 1/1989 | Abraham et al. |
| 5,352,315 A | 10/1994 | Carrier et al. |
| 5,354,790 A | 10/1994 | Keusch et al. |
| 5,480,399 A * | 1/1996 | Hebborn .................. 606/35 |
| 5,520,683 A | 5/1996 | Subramaniam et al. |
| 5,830,212 A | 11/1998 | Cartmell et al. |
| 5,836,942 A | 11/1998 | Netherly et al. |
| 6,053,910 A | 4/2000 | Fleenor |
| 6,083,221 A | 7/2000 | Fleenor et al. |
| 6,454,764 B1 * | 9/2002 | Fleenor et al. ............ 606/32 |
| 6,547,786 B1 | 4/2003 | Goble |
| 6,666,859 B1 | 12/2003 | Fleenor et al. |
| 7,169,145 B2 | 1/2007 | Isaacson et al. |
| 2005/0101947 A1 | 5/2005 | Jarrard et al. |

FOREIGN PATENT DOCUMENTS

| | | |
|---|---|---|
| GB | 2 052 269 | 1/1981 |
| JP | S55-168317 | 5/1979 |
| JP | S57-154409 | 9/1982 |
| JP | S57-188250 | 11/1982 |
| JP | S63-54148 | 3/1988 |

OTHER PUBLICATIONS

Notice of Allowance dated Jul. 13, 2006, 4 pages, U.S. Appl. No. 10/719,333.

Non-Final Office Action dated Aug. 24, 2005, 4 pages, U.S. Appl. No. 10/719,333.

Notice of Allowance dated Dec. 12, 2005, 6 pages, U.S. Appl. No. 10/719,333.

* cited by examiner

TUNED RETURN ELECTRODE WITH MATCHING INDUCTOR

RELATED APPLICATIONS

This application is a continuation application of co-pending U.S. patent application Ser. No. 10/719,333, filed 21 Nov. 2003, entitled "Tuned Return Electrode with Matching Inductor", the disclosure of which is incorporated herein by this reference.

BACKGROUND OF THE INVENTION

1. The Field of the Invention

The present invention relates generally to electrosurgical systems. More specifically, the present invention relates to electrosurgical electrodes that are adapted for providing safe and effective electrosurgery.

2. The Relevant Technology

As is known to those skilled in the art, modern surgical techniques typically employ radio frequency (RF) power to cut tissue and coagulate bleeding encountered in performing surgical procedures. For historical perspective and details of such techniques, reference is made to U.S. Pat. No. 4,936,842, issued to D'Amelio et al., and entitled "Electroprobe Apparatus," the disclosure of which is incorporated by this reference.

As is known to those skilled in the medical arts, electrosurgery is widely used and offers many advantages including the use of a single surgical tool for both cutting and coagulating the tissue of a patient. Every monopolar electrosurgical generator system must have an active electrode that is applied by the surgeon to the patient at the surgical site and a return path from the patient back to an electrosurgical generator that provides the RF power used during electrosurgical procedures. The active electrode at the point of contact with the patient must be small to produce a high current density resulting in a surgical effect of cutting or coagulating tissue. The return electrode, which carries the same current as the active electrode, must be large enough in effective surface area at the point of communication with the patient so that the density of the electrosurgical current flowing from the patient to the return electrode is limited to safe levels. If the density of the electrosurgical current is relatively high at the return electrode, the temperature of the patient's skin and tissue will rise in this area and can result in an undesirable patient burn.

In 1985, the Emergency Care Research Institute, a well-known medical testing agency, published the results of testing it had conducted on electrosurgical return electrode site burns, stating that the heating of body tissue to the threshold of necrosis occurs when the current density exceeds 100 milliamperes per square centimeter. The Association for the Advancement of Medical Instrumentation ("AAMI") has published standards that require that the maximum patient surface tissue temperature adjacent an electrosurgical return electrode should not rise more than six degrees (6E) Celsius under stated test conditions.

Over the past twenty years, products have been developed in response to the medical need for a safer return electrode. One advancement in return electrode technology was the development of a flexible electrode to replace the small, about 12×7 inches, flat stainless steel plate electrode typically in use during electrosurgical procedures. This plate electrode was typically coated with a conductive gel, placed under the patient's buttocks, thigh, shoulders, or any other location, and relied upon gravity to ensure adequate contact area. These flexible electrodes, which are generally about the same size as the stainless steel plates, are coated with a conductive or dielectric polymer and have an adhesive border on them so they will remain attached to the patient without the aid of gravity. By the early 1980's, most hospitals in the United States were using flexible electrodes. Flexible electrodes resulted in fewer patient return electrode burns but resulted in additional surgical costs in the United States of several tens of millions of dollars each year because each electrode had to be disposed of after use. Even with this improvement, hospitals were still experiencing some patient burns caused by electrodes that would accidentally fall off or partially separate from the patient during surgery.

In an attempt to minimize the potential for patient burns, contact quality monitoring systems were developed. Contact quality monitoring systems are adapted to monitor the contact area of an electrode that is in contact with a patient and turn off the electrosurgical generator whenever there is insufficient contact area between the patient and the electrode. Such circuits are shown, for example, in U.S. Pat. No. 4,200,104 issued to Harris, and entitled "Contact Area Measurement Apparatus for Use in Electrosurgery" and; U.S. Pat. No. 4,231,372, issued to Newton, and entitled "Safety Monitoring Circuit for Electrosurgical Unit," the disclosures of which are incorporated by this reference. Contact Quality Monitoring Systems have resulted in additional reduction in patient return electrode burns, but require special disposable electrodes, resulting in an increase in the cost per procedure. Twenty years after these systems were first introduced, only 75 percent of all the surgical operations performed in the United States use contact quality monitoring systems because of the increased costs and other factors.

Self-limiting electrosurgical return electrodes provide an alternative to contact quality monitoring systems. Self-limiting electrosurgical return electrodes allow electrosurgery to be performed when the contact area between the patient and the pad is sufficient to limit the current density of the electrosurgical current to safe levels and when there are not too many materials placed between the patient and the pad. When the contact area between the patient and the return electrode falls below a minimum contact area or when too many materials are placed between the patient and the pad, the properties of the pad limit the flow of current to prevent a patient burn.

While self-limiting electrodes are typically reusable and provide current limiting when the contact area between the patient and the electrode falls below a minimum contact area or too many materials are placed between the patient and the pad, the impedance properties of the pad can result in current limiting of the electrosurgical current under some conditions. For example, during surgeries that require high current flow such as trans-urethral resection of the prostate procedures (TURP), though the contact area may be sufficient to conduct safe electrosurgery, small increases in impedance can noticeably affect the current flow. Additionally, procedures involving small pediatric patients can result in diminished current flow due to the relatively small contact area of the patient with the pad and the resulting increases in impedance. This is particularly true for neonatal patients, where the small size and mass of the patients have rendered present applications impractical.

BRIEF SUMMARY OF THE INVENTION

The present invention is directed to an electrosurgical return electrode adapted to prevent patient burns. The return electrode provides a bulk impedance that provides self-limiting properties to the electrode. The bulk impedance of the electrosurgical return electrode allows the return electrode to be self-limiting and can result from the properties of the semi-insulating member, the conductor member, a combination of both the semi-insulating member and the conductor member, or a combination of two or more of the semi-insulating member, the conductor, clothing of the patient, blankets, sheets, and other materials that are disposed between the patent and the return electrode.

According to one aspect of the present invention, an inductor is coupled in series with a capacitive electrosurgical return electrode. The inductor is configured to optimize the flow of the electrosurgical current by minimizing the effective impedance of the electrosurgical return electrode when the amount of contact area between the patient and the electrosurgical return electrode is sufficient to conduct electrosurgery or where materials are placed between the patient and the electrosurgical return electrode.

According to another aspect of the present invention, a capacitor is coupled in series with an inductive electrosurgical return electrode. The capacitor is configured to optimize the flow of the electrosurgical current by minimizing the effective impedance of the electrosurgical return electrode when the amount of contact area between the patient and the electrosurgical return electrode is sufficient to conduct electrosurgery or where materials are placed between the patient and the electrosurgical return electrode.

According to another aspect of the present invention, the electrosurgical return electrode has a bulk impedance sufficient to prevent a patient burn when the contact area between the patient and the electrode is below a given threshold. The conductor member is adapted for use with circuitry that indicates to a user when the contact area between the patient and the self-limiting member and/or return electrode is below a given threshold.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof that are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

An electrosurgical return electrode is provided having a bulk impedance sufficient to prevent a patient burn when the contact area between the patient and the electrode is below a given threshold. According to one aspect of the invention, an inductor is coupled in series with a capacitor as part of an electrosurgical circuit. In the embodiment, the electrosurgical return electrode can comprise a capacitive electrosurgical return electrode that is utilized with a series inductor. Alternatively, the electrosurgical return electrode can comprise an inductive electrosurgical return electrode that is utilized with a series capacitor. Where a series inductor is utilized, the inductor is configured to optimize the flow of the electrosurgical current by minimizing the effective bulk impedance of the electrosurgical return electrode when the amount of contact area between the patient and the electrosurgical return electrode is sufficient to conduct electrosurgery. According to another aspect of the present invention, a conductor member is adapted for use with circuitry that indicates to a user when the contact area between the patient and the return electrode is below a given threshold.

Series Inductor

With reference now to FIGS. 1-7, consider a capacitive electrosurgical return electrode utilized with a series inductor to minimize the effective impedance of the electrosurgical return electrode. While a complete discussion of the series capacitor for use with an inductive electrosurgical return electrode is not included, as will be appreciated by those skilled in the art, the principles discussed with reference to the series inductor employed with a capacitive electrosurgical return electrode can be utilized to minimize the bulk impedance of an inductive electrosurgical return electrode with a series capacitor.

Figure 1:
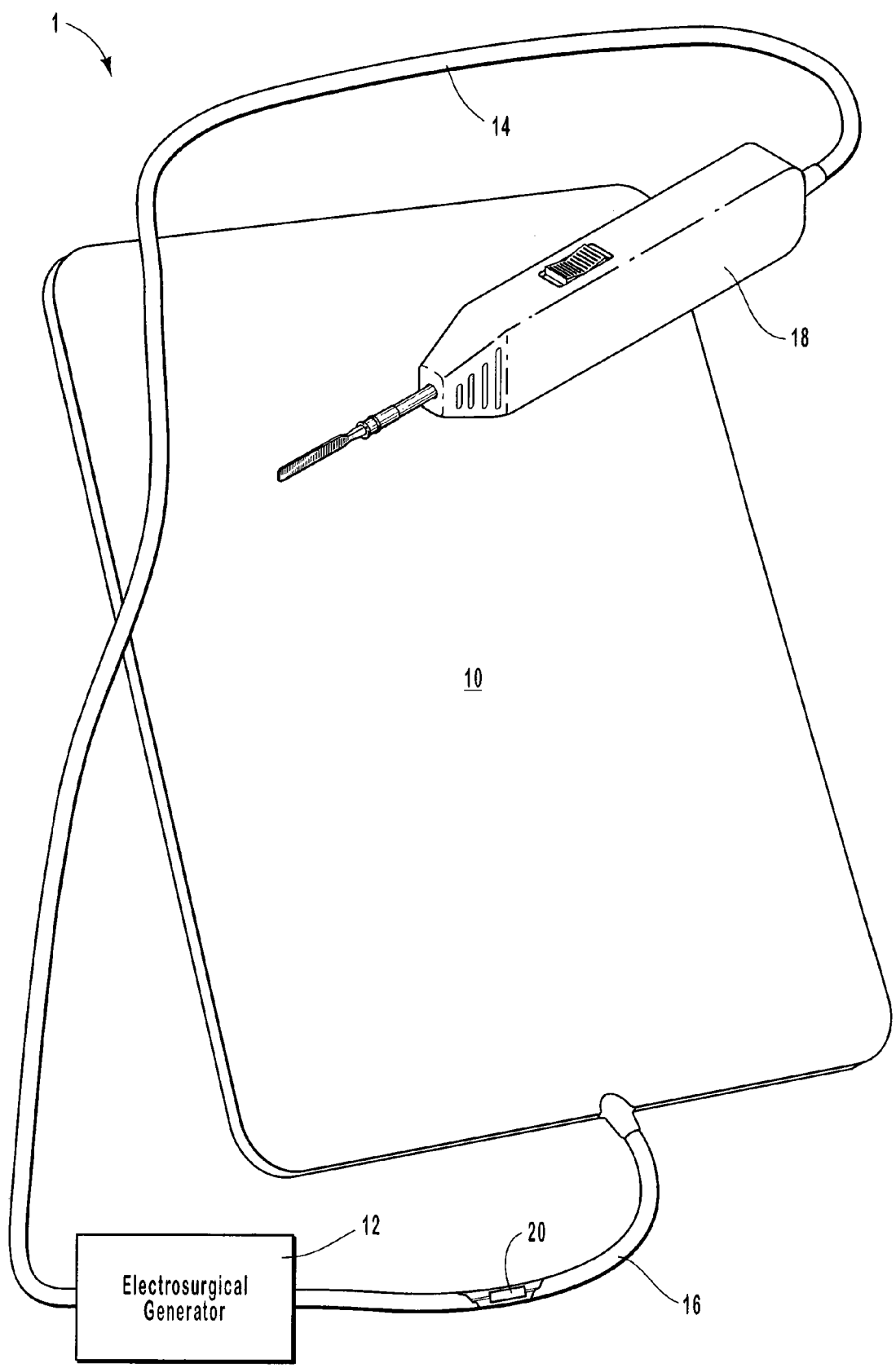
FIG. 1 is a perspective view of an electrosurgical system illustrating an inductor connected in series with an electrosurgical return electrode.

With reference now to FIG. 1, there is shown an electrosurgical system 1 having an inductor coupled in series with a return electrode to minimize the effective bulk impedance of the return electrode. As depicted, system 1 includes a return electrode 10, an electrosurgical generator 12, and an inductor 20. There is also shown a member 14, a member 16, and an electrosurgical tool 18. Electrosurgical generator 12 generates an electrosurgical current (i.e. radio frequency (RF) energy) that is conveyed to electrosurgical tool 18 by means of member 14. Electrosurgical tool 18 is configured to utilize the electrosurgical current during a procedure to cut and coagulate tissue of a patient resting on the return electrode 10. Various types of electrosurgical generator 12 are known to those skilled in the art in light of the teaching contained herein. The electrosurgical current is returned to electrosurgical generator 12 utilizing member 16 as the return path. In the illustrated embodiment, members 14 and 16 comprise cabling that operate as conductors of the electrosurgical current.

Return electrode 10 is adapted to limit the density of electrosurgical current flowing from a patient resting on the return electrode 10 back to the electrosurgical generator. Return electrode 10 is adapted to provide self-limiting properties to prevent patient burns. The self-limiting properties of return electrode 10 effectively increase the effective impedance of return electrode 10 to reduce current from flowing when there is insufficient contact area between the patient and return electrode 10. By reducing current from flowing, use of electrosurgical tool 18 is inhibited and the possibility of patient burns is minimized. Illustrative materials and geometries for return electrode 10 are described in U.S. Pat. No. 6,454,764 entitled "Self-Limiting Electrosurgical Return Electrode" and other related patent applications, the disclosures of which is incorporated herein by reference.

Inductor 20 is connected in series with electrosurgical electrode 10. Inductor 20 is configured to minimize the effective impedance of the electrosurgical current when the amount of contact area between the patient and the electrosurgical return electrode is sufficient to conduct electrosurgery, thus optimizing the flow of the electrosurgical current. As will be appreciated by those skilled in the art, the relationship between the power delivered by an electrosurgical current and the impedance of an electrosurgical current is depicted by a power curve. The power curve indicates that as the impedance of the electrosurgical circuit increases the power delivered by the electrosurgical current decreases. The specific relationship between the power delivered and the impedance is dependent on the properties of the components of the electrosurgical circuit. Because the impedance at the surgical interface is an important source of impedance in an electrosurgical circuit, the effective impedance of the electrosurgical return electrode largely determines the amount of power delivered by the electrosurgical current. The impedance of the electrosurgical return electrode can be the product of one or a combination of a resistive component, a capacitive component, and an inductive component. Inductor 20 is capable of reducing the overall impedance of the electrosurgical circuit by counteracting the capacitive component of the effective impedance of the electrosurgical return electrode. Reduced overall impedance of the electrosurgical circuit results in increased flow of electrosurgical current and a resultant increase in power delivered by the electrosurgical current.

A variety of different types and configurations of inductors can be utilized in light of the present invention including, but not limited to, a solid state inductor, or an electromechanical inductor. In the illustrated embodiment inductor 20 is coupled to member 14. As will be appreciated by those skilled in the art, inductor 20 can be placed in a variety of positions within the system and in a variety of configurations without departing from the scope and spirit of the present invention. For example, the conductor can be placed in member 16, electrosurgical tool 18, or electrosurgical generator 12.

Figure 2:
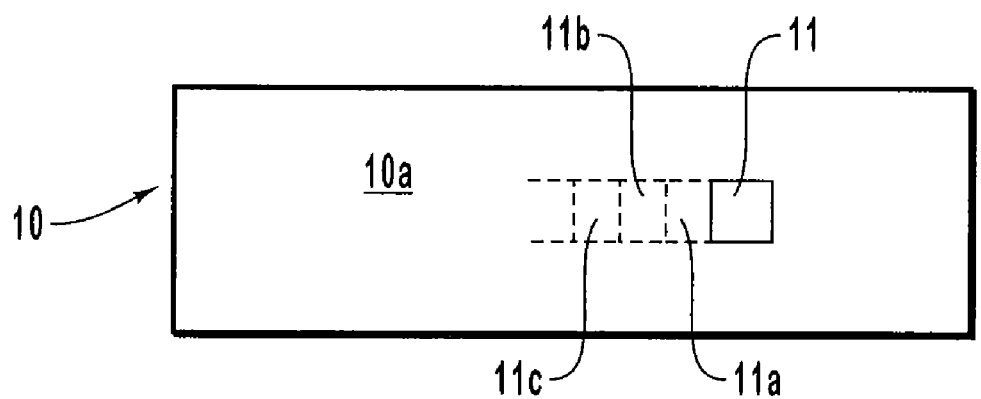
FIG. 2 is a top view of a return electrode illustrating the principles by which impedance varies as a function of contact area.

Now turning to FIG. 2, there will be seen a schematic representation of the top view of a return electrode 10 illustrating the self-limiting principles of return electrode 10. The effective impedance of return electrode 10 and its relationship to self-limiting principles illustrates the manner in which an inductor can be utilized to minimize the effective impedance of the electrosurgical return electrode. For instructional purposes of this description and to aid in the mathematical modeling of electrode 10, electrode 10 may be thought of as including a plurality of uniformly sized, continuous regions or segments as represented by regions $11a, 11b, 11c \ldots 11n$. One skilled in the art will appreciate, however, that electrode 10 may include discontinuous regions or segments.

It is known that, in contrast with the series circuit, combined resistive and capacitive reactances, when connected in parallel, present a total effective impedance that is given by the formula:

$$z_{\mathit{eff}} = \frac{1}{\frac{1}{z_1} + \frac{1}{z_2} + \frac{1}{z_3} + \frac{1}{z_4} + \frac{1}{z_5} + \frac{1}{z_6}} \quad (1)$$

Thus, if 100 similar impedances, each of 100 ohms, were connected in parallel, the effective impedance $Z_{\mathit{eff}}$ would equal one ohm. If half of such impedances were effectively disconnected, the remaining effective impedance would be two ohms, and if only one of the impedances were active in the circuit, the remaining effective impedance would be 100 ohms. As a result, the total effective impedance of electrode 10 is rendered self-limiting due to properties of capacitors, resistors, and inductors in parallel.

Each of the segments of electrode 10 corresponding to segments $11a \ldots 11n$ inherently has the capability of presenting an impedance. However, the number of such segments that are effectively active in parallel within the circuit is a direct function of the surface area of the patient that overlies the electrode. Thus, in the case of a large supine patient whose body is in effective contact with 50 percent (50%) of the upper surface of electrode, 50 percent of the segments corresponding to segments $11a$-$11n$ will be effectively in parallel in the circuit to form a given impedance. Where electrode 10 contains 100 segments of 1000 ohms each, the effective impedance operatively presented by the effective 50 percent of the electrode elements would be 20 ohms. Since 20 ohms is very small compared with the impedance at the surgical interface, very little energy is dissipated at the region of contact between the patient and electrode 10, and due also to the relatively large effective working area of electrode 10, current density, and temperature elevation are maintained below the danger thresholds mentioned above.

Now, if for any reason, the effective contact area between the patient and electrode 10 were to be reduced to the surface of only one of segments $11a$-$11n$, then the effective impedance would increase to 1000 ohms. At some point of reduction in contact area, the effective impedance would rise to a level relative to the impedance presented at the site of electrosurgical tool or instrument 18 (FIG. 1) to diminish the electrosurgical effect of tool or instrument 18 or otherwise prevent effective use of tool or instrument 18 by the surgeon. This diminishing of electrosurgical effect or effectiveness of tool or instrument 18 signals to the surgeon that the patient should be repositioned so as to present a greater surface area in contact with return electrode 10. As the effective impedance rises, the total circuit impedance would be increased so that the total current that would flow if the surgeon attempted to employ tool or instrument 18 without repositioning the patient would be reduced to a value below that which would cause undesired trauma to the patient.

When the effective contact area is large, the current at the surgeon's implement is high and the corresponding current density across return electrode 10 low. This is the condition desired for performing surgery. However, as the effective surface area decreases, the impedance of return electrode 10 increases with a corresponding decrease in the current at tool or instrument 18 (FIG. 1). When the effective surface area declines to some predetermined point, there will remain insufficient current at tool or instrument 18 to effectively conduct surgery. The parameters selected for the materials and dimensions of electrode 10 are chosen so that current density and corresponding tissue temperature elevation adjacent return electrode 10 does not exceed the limits mentioned in the introduction hereof. For example, in one embodiment return electrode 10 has a bulk impedance of at least 4,000 $\Omega\cdot$cm so as to limit the current density to safe levels. To facilitate description of the principles underlying the invention, the foregoing is described in terms of impedances whose principal components are resistances and capacitive reactances. However, the principles of the invention are also applicable to other embodiments in which the impedances include any combination of resistive, capacitive and/or inductive impedances.

By providing a return electrode 10 having both the desired bulk impedance and a sufficient surface area, the electrosurgical current is distributed sufficiently such that the current density does not result in a patient burn. It has been found that with selected materials and geometries, the self-limiting principles hereof can be achieved in a return electrode as small as about seven square inches (or about 45 square centimeters) in working surface area, while the preferable range of exposed upper working surface area of return electrode 10 lies in the range of from about 11 to 1,500 square inches (or about 70 to 9,680 square centimeters).

Return electrode 10 need not be in direct physical contact with the patient. Having a working surface area of this size eliminates the need for direct physical attachment, either directly to the skin of the patient or through gels. A patient can be in electrical connection with return electrode 10 without requiring the use of adhesives or gels. This also allows return electrode 10 to be re-used thereby eliminating the need and cost of disposable split-plate electrodes that are commonly used. This reduces the cost for using contact quality monitoring techniques to verify that the patient is sufficiently in contact with a return electrode to prevent high current densities that result in patient burns.

Additionally, it can be understood that the self-limiting characteristics or capabilities of return electrode 10 can be achieved where return electrode 10 is substantially enclosed within a semi-insulating member. Additionally, the self-limiting characteristics or capabilities can be provided in part, from materials, members or elements disposed between return electrode 10 and a patient. For instance, such other materials, members, or elements can include but are not limited to, sheets, clothing, blankets, or the like. Therefore, electrode 10 has an effective bulk impedance sufficient to prevent a patient burn when the contact area between the patient and electrode 10 is below a given threshold.

The electrode 10 according to the invention hereof may be made of conductive plastic, rubber, or other flexible material which, when employed in electrode 10 will result in an effective DC resistance presented by each square centimeter of working surface sufficient to limit the current density to safe levels. Silicone or butyl rubber have been found to be particularly attractive materials as they are flexible, as well as readily washable and sterilizable. Alternatively, a portion of return electrode 10 may be made of inherently relatively high resistance flexible material altered to provide the requisite conductivity. For example, a silicone rubber material in which there are impregnated conductive fibers, such as carbon fiber, or in which there have been distributed quantities of other conductive substances such as carbon black, quantities of gold, silver, nickel, copper, steel, iron, stainless steel, brass, aluminum, or other conductors. A more complete discussion of self-limiting characteristics can be found in U.S. Pat. No. 6,454,764 entitled "Self-Limiting Electrosurgical Return Electrode," which is incorporated herein by reference.

Figure 3:
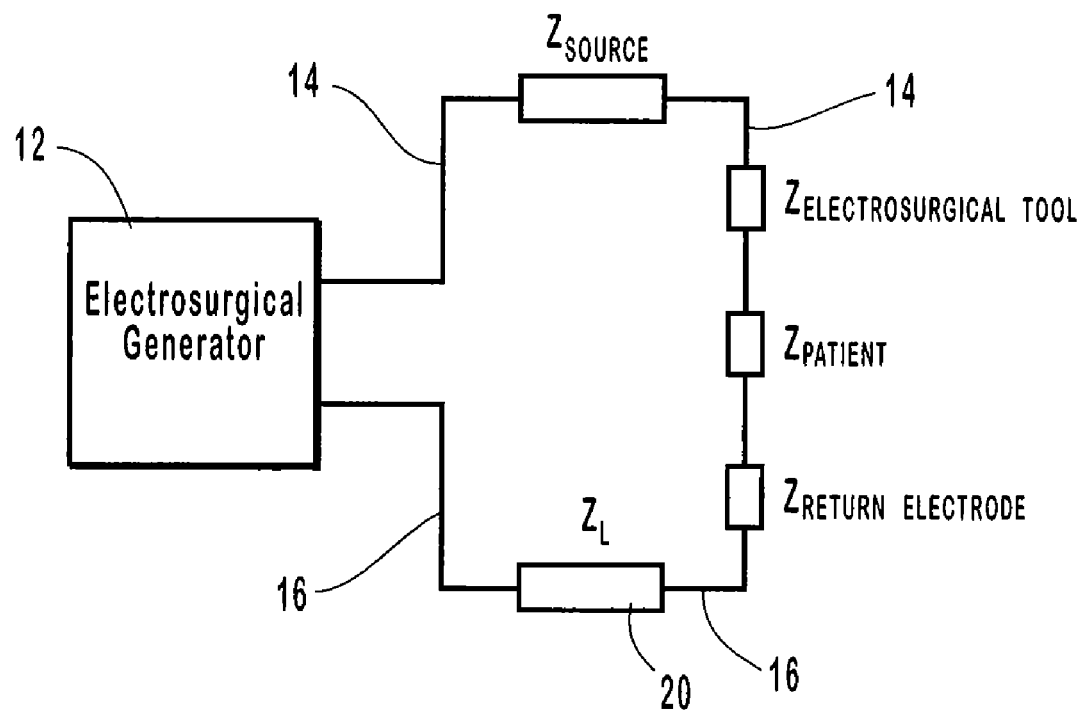
FIG. 3 is a schematic view illustrating the impedances presented to an electrosurgical current and inductor coupled in series therewith.

With reference now to FIG. 3, there is shown a simplified electrical schematic diagram of an electrosurgical circuit illustrating the manner in which an inductor can be utilized to minimize the effective impedance of a return electrode. There are shown the typical impedances $z_1$, $z_2$, and $z_3$ effectively included in the operative path of an electrosurgical current during an operative procedure and an inductor 20 connected in series therewith. The inductor 20 is configured to minimize the effective impedance of the electrosurgical return electrode when the amount of contact area between the patient and the electrosurgical return electrode is safe with regard to current densities.

Electrosurgical generator 12 is adapted to provide an electrosurgical current, such as but not limited to constant flow, voltage, and/or current or variable flow, voltage and/or current. Connected to electrosurgical generator 12 are conventional electrical conductors 14 and 16 which respectively connect the generator 12 to the electrosurgical tool 18 represented by impedance $z_1$ (at the surgical interface) and an return electrode 10 represented by impedance $z_3$. Impedance $z_2$ is provided to represent the impedance presented by the patient's tissue lying between the operation site and the return electrode.

The diagram of FIG. 3 is a simplified version of the electrosurgical current circuit. The diagram generally considers circuit elements in terms of the principal impedances, including the impedances contributed by the surgical interface, the patient's body, and the return electrode, so as to clearly and succinctly illustrate principles of the invention, it should be understood that in reality certain other parameters would be encountered, parameters such as distributed inductance and distributed capacitance which, for purposes of clarity in illustration of the principles hereof, are deemed relatively small and so are not considered in this description.

The initial embodiment, hereof, is that of an electrode operating in an exclusive capacitive mode or a combined resistive and capacitive mode. Accordingly, if the relatively small stray capacitive and inductive reactances are disregarded, the total effective impedance of the circuit will be equal to the sum of the individual impedances $z_1$, $z_2$ and $z_3$ minus the series inductor; and since essentially the same current will pass through all three, the voltage generated by electrosurgical generator 12 will be distributed across impedances $z_1$, $z_2$ and $z_3$ in direct proportion to their respective values. Thus, the energy dissipated in each of such components will also be directly proportional to their values.

Since it is desired that developed energy be concentrated in the region where the surgeon's implement contacts the patient's tissue, it is desirable that the resistive component of the impedance represented by $z_1$ be substantial and that current passing therethrough (and consequent energy dissipation) be concentrated in a very small region. The latter is accomplished by making the region of contact with the patient at the operative site very small.

In contrast to the region where the surgeon's implement contacts the patient's tissue, it desired that the effective impedance $z_3$ of the return electrode be minimized and that the current passing therethrough be distributed in a large region to avoid an undesirable patient burn. Accordingly, it is desired that the contact area between the patient and the return electrode 10 be substantial (compared to the region where the surgeon's implement contacts the patient's tissue) and the effective impedance of the return electrode be small. Return electrode 10 is rendered self-limiting to ensure that the current density of the current passing therethrough is limited so as not to result in a patient burn. As will be appreciated by those skilled in the art, a variety of combinations of resistive components, capacitive components, and/or inductive components can be utilized to achieve the self-limiting characteristics or capabilities of return electrode 10.

As previously discussed, inductor 20 is coupled in series with return electrode 10 and impedance $z_3$ presented thereby. Inductor 20 is configured to counteract the capacitive component of the effective impedance $z_3$ of the electrosurgical return electrode. The impedance of the return electrode 10 can be presented by a resistive component, a capacitive component, and/or an inductive component, as shown by the following equations:

$$X_c = \frac{1}{j\omega C} \quad (1)$$

where $X_c$ is the capacitive reactance, j is the vector direction of the capacitive reactance and is equal to $1/\sqrt{-1}$, $\omega$ is the frequency in Hertz of the electrosurgical current multiplied by $2\pi$, C is the capacitance in Farads;

$$X_L = j\omega L \quad (2)$$

Where $X_L$ is the inductive reactance, j is the vector direction of the inductive reactance and is equal to $1/\sqrt{-1}$, $\omega$ is the frequency in Hertz of the electrosurgical current multiplied by $2\pi$, and L is the inductance in millihenrys (mH). The total impedance of return electrode 10 is the sum of the resistive component, the capacitive component, and the inductive component and is given by the formula:

$$Z_{tot} = R + \frac{1}{j\omega C} + j\omega L \quad (3)$$

By changing the phase angle (represented by the symbol j), it is possible to utilize the inductive reactance to reduce the amount of capacitive reactance of the electrosurgical electrode, as shown in the following equation:

$$Z_{tot} = R + \frac{1}{j}\left(\frac{1}{\omega C} - \omega L\right) \quad (4)$$

Equation 5 illustrates that, by changing the phase of the inductive reactance, the phase angle can be factored out of the inductive and capacitive reactances. Once the phase angle is factored out, the inductive reactance can be subtracted from the capacitive reactance. Thus, by changing the phase angle expression of the inductive reactance, the inductive reactance can be utilized to counteract the effective capacitive reactance presented by the return electrode 10. In other words, the phase angle of the inductance can be utilized to minimize the capacitive reactance of the parallel plate capacitor when the amount of contact area between the patient and the electrosurgical return electrode is sufficient to limit the density of the electrosurgical current to safe levels.

Figure 4:
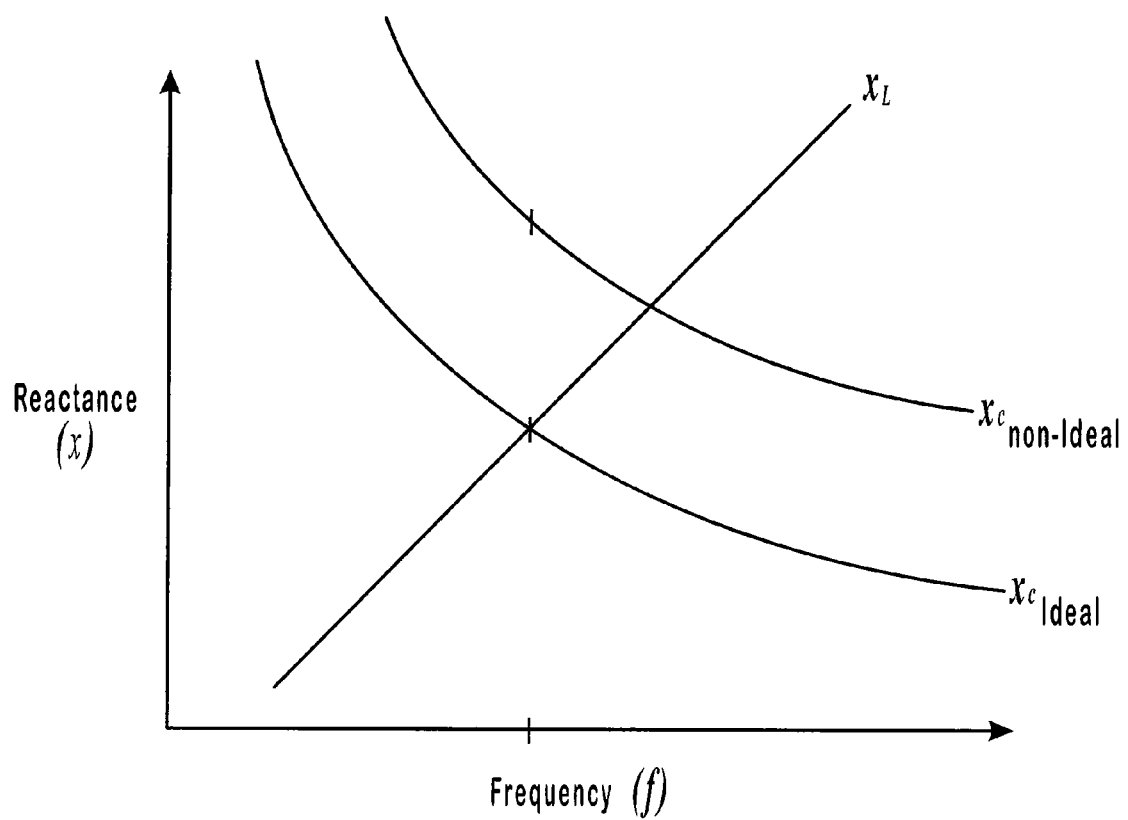
FIG. 4 is a chart illustrating in graphical form the relationship between capacitive reactance, inductive reactance, and frequency of an electrosurgical current.

With reference now to FIG. 4, there is shown the relationship between frequency of an electrosurgical current flowing through the return electrode and the reactance of a capacitor and an inductor. However, before proceeding to a consideration of such chart, it should be noted that the chart is simplified so as to illustrate the principles underlying the invention and does not represent actual data that may vary substantially. The graph illustrates that the magnitude of the inductive reactance and capacitive reactance vary according the frequency of the electrosurgical current. The inductive reactance varies in proportion to the frequency of the electrosurgical current, while the capacitive reactance varies in inverse proportion to the frequency of the electrosurgical current. This is due to the fact that inductive reactance and capacitive reactance are determined using $\omega$ represented by the equation:

$$\omega = 2\pi f \quad (5)$$

where $\pi$ is 3.14159, f is frequency in hertz.

Where the frequency of the electrosurgical current is constant, the amount of inductive reactance can be established by simply selecting an inductor 20 having a desired amount of inductance. Due to the fact that electrosurgical generators typically provide an electrosurgical current having a consistent frequency, the frequency is an ascertainable constant. Where the capacitance of the parallel plate capacitor and the frequency are also known, a selected inductive reactance can be utilized to minimize the orthogonal reactance of the return electrode 10 relative to resistance. However, the capacitive reactance can be difficult to establish due to the fact that the self-limiting electrode is typically utilized such that the amount of contact area between the patient and the return electrode is variable. Additionally, the capacitive reactance can be affected by materials positioned between the patient and the electrosurgical return electrode. The relationship between contact area, interposed materials, and capacitive reactance is discussed in greater detail with reference to FIGS. 5A and 5B.

In selecting a desired amount of inductive reactance, a user can determine an ideal capacitive reactance $X_{cIdeal}$ based on the desired contact area and properties of the materials between the patient and the electrosurgical return electrode. The relationship of capacitive reactance for $X_{cIdeal}$ relative to frequency is depicted in FIG. 4. Once the amount of capacitive reactance for $X_{cIdeal}$ is determined for the frequency of the electrosurgical generator, an inductor can be selected that provides a desired amount of inductive reactance to counteract the capacitive reactance of $X_{cIdeal}$. The point of intersection of $X_{cIdeal}$ and $X_L$ indicates the frequency where the reactances of $X_{cIdeal}$ and $X_L$ counteract one another. As a result, where the actual capacitive reactance of the electrosurgical circuit is $X_{cIdeal}$, the series inductor will counteract the capacitive reactance and the overall impedance will be reduced by the magnitude of the capacitive reactance.

However, where the contact area and/or the materials between the patient and the electrosurgical return electrode vary from the desired contact area and/or the desired properties of the materials between the patient and the electrosurgical return electrode, the capacitive reactance will vary from $X_{cIdeal}$ as is shown with respect to $X_{cnon-ideal}$. Where the capacitive reactance is represented by $X_{cnon-ideal}$ rather than by $X_{cIdeal}$, the inductive reactance will continue to counteract the capacitive reactance presented by the electrosurgical circuit. However, the reduction in the overall impedance will not be reduced by the magnitude of the actual capacitive reactance of the circuit. Instead, the overall impedance of the electrosurgical circuit will be reduced by an inductive reactance provided by the inductor that is different from the magnitude of the actual capacitive reactance of the electrosurgical circuit. Where the capactive reactance is greater than inductive reactance, as with $X_{cnon-ideal}$, a reduced net positive capacitive reactance will be produced. Where the capacitive reactance is less than the inductive reactance, a net inductive reactance will be produced.

As will be appreciated by those skilled in the art, a series capacitor can be utilized with a self-limiting electrosurgical return electrode having an inductive component without departing from the scope and spirit of the present invention. A series capacitor can be utilized relying on the principles describe with reference to FIG. 4. In the embodiment, the series capacitor provides a level of capacitive reactance needed to counteract the inductive reactance of the electrosurgical return electrode. A variety of type and configuration of the series capacitors can be utilized without departing from the scope and spirit of the present invention.

Figure 5A:
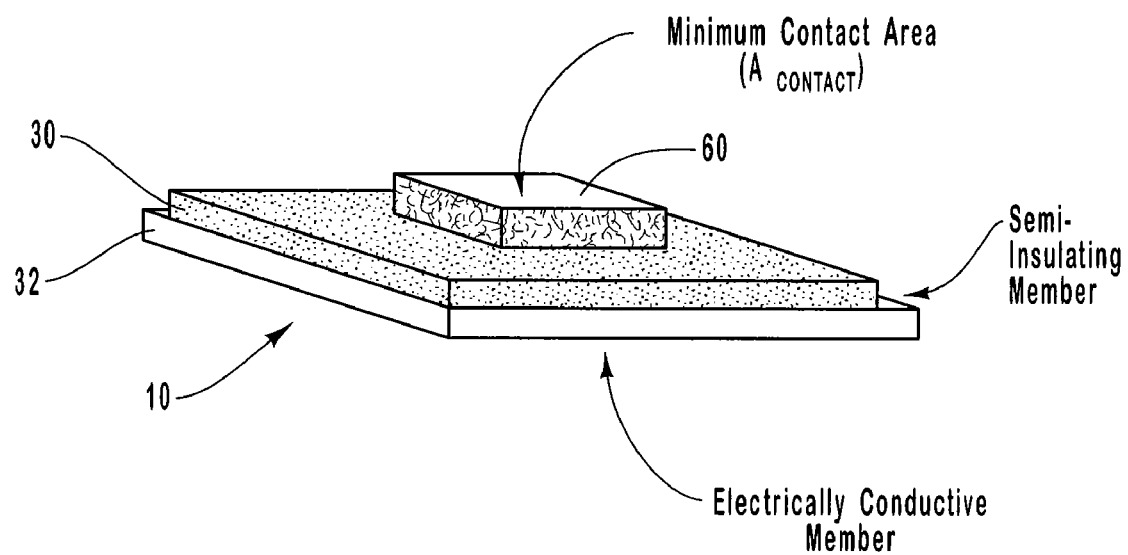
FIG. 5A is a perspective view illustrating a representative patient in contact with a semi-insulating member of a return electrode.

With reference now to FIG. 5A, there is shown a schematic representation of return electrode 10 and a patient in contact therewith. FIG. 5A is utilized to illustrate the relationship between the contact area and the capacitive reactance in order to describe how an inductor can be utilized to minimize the capacitive reactance of the return electrode while maintaining the self-limiting properties of the return electrode 10. There is shown a conducting layer 60 and a return electrode 10. In the illustrated embodiment, return electrode 10 comprises a semi-insulating member 30 and an electrically conductive member 32. Conducting layer 60 represents a patient resting on a semi-insulating member 30. Conducting layer 60 is configured to represent the minimum contact area required to limit the current density to safe levels.

As discussed with reference to FIG. 2, the number of such segments that are effectively active in parallel within the circuit is a direct function of the surface area of the patient that overlies return electrode 10. Where the surface area of the patient that overlies electrode 10 is at, or above, the minimum contact area, the total effective impedance is sufficiently low to permit the electrosurgical current to conduct safe and effective electrosurgery. Where the impedance is due primarily to a capacitive component and a resistive component, the amount of impedance is inversely proportional to the amount of patient contact area.

While the effective impedance is sufficiently low to conduct safe electrosurgery, under some conditions the effective impedance resulting from the contact area and the properties of the pad can result in current limiting of the electrosurgical current. This is often the result of a bulk impedance of the pad that exceeds 10,000 ohms centimeter. For example, during surgeries that require high current flow such as trans-urethral resection of the prostate procedures (TURP), small increases in impedance can noticeably affect the current flow. Additionally, procedures involving small pediatric patients can result in diminished current flow due to the contact area of the patient with the pad and the resulting increases in impedance. This is particularly true for neonatal patients, where the small size and mass of the patients have rendered present applications impractical.

By placing inductor 20 (see FIG. 1) in series with return electrode 10, the effective impedance of the return electrode can be minimized. For example, during surgeries that require high current flow, inductor 20 can counteract the capacitive reactance component of the effective impedance of the return electrode. By counteracting the capacitive reactance, only the resistive component of the bulk impedance remains (assuming little or no inductive reactance in the return electrode.) The capacitive reactance is a function of several factors including the contact area of the patient to the return electrode. Where the patient contact area is greater than, or equal to, the minimum contact area, or where the materials between the patient and the electrosurgical return electrode are minimal, the effective impedance of the return electrode is often in the range of 100 ohms. The inductor is configured to reduce the effective impedance of the electrosurgical electrode below 100 ohms. Where the majority of the effective impedance of the return electrode is due to capacitive reactance, an inductor providing a desired amount of inductance can be utilized to eliminate the majority of the effective impedance of the return electrode. By minimizing the effective impedance of the pad, surgeries that are sensitive to small changes in the effective impedance of the return electrode, such as pediatric, neonatal, and TURP procedures can be performed with minimal reduction in the current flow.

The capacitive reactance of the return electrode is determined in order to identify the amount of inductance to be provided by the inductor. As previously discussed, the capacitive reactance of a split electrode is defined by the equation:

$$X_c = \frac{1}{j\omega C} \quad (6)$$

While the frequency of a self-limiting return electrode can be controlled without difficulty, the amount of capacitance C can be more complicated to control.

The capacitance for a parallel plate capacitor is defined as:

$$C = \frac{K\varepsilon_0 A}{t} \quad (7)$$

where C is capacitance in Farads, κ is the dielectric constant of the material lying between the effective plates of the capacitor, A is the area of the smallest one of the effective plates of the capacitor in square meters, t is the separation of the surfaces of the effective plates in meters, and $\epsilon_0$ is the permittivity of air in Farads/meter. There are two primary mechanisms by which the capacitance C can be varied: 1) patient contact area A (i.e. the area of the smallest one of the effective plates of the capacitor in square centimeters); and 2) materials lying between the patient and the return electrode (i.e. which can affect both κ the dielectric constant of the material lying between the effective plates of the capacitor and t the separation of the surfaces of the effective plates in meters.) By providing parameters to control the variability in materials positioned between the patient and the return electrode 10, κ the dielectric constant of the material lying between the effective plates of the capacitor, $\epsilon_0$ the permittivity of air in Farads/meter, and t the separation of the surfaces of the effective plates in meters will all be constants. However, due to the manner in which return electrode 10 will typically be utilized, the patient contact area A (i.e. the area of the smallest one of the effective plates of the capacitor in square centimeters) will be variable. As will be appreciated by those skilled in the art, the area of the smallest one of the effective plates of the capacitor is the equivalent of the contact area between the patient and the return electrode.

Due to the self-limiting aspects of return electrode 10 and the manner in which the self-limiting return electrode 10 is utilized, the contact area between the patient and the return electrode will vary during the course of a medical procedure. The bulk impedance of the pad allows a user to counteract the capacitive component of the effective bulk impedance of the electrosurgical return electrode 10 when the amount of contact area is safe with respect to current densities while maintaining the self-limiting aspect of the return electrode when the contact area is reduced. The ability to counteract the orthogonal impedance of the return electrode while maintaining the self-limiting aspect of the return electrode is shown in greater detail with reference to FIG. 5B.

Figure 5B:
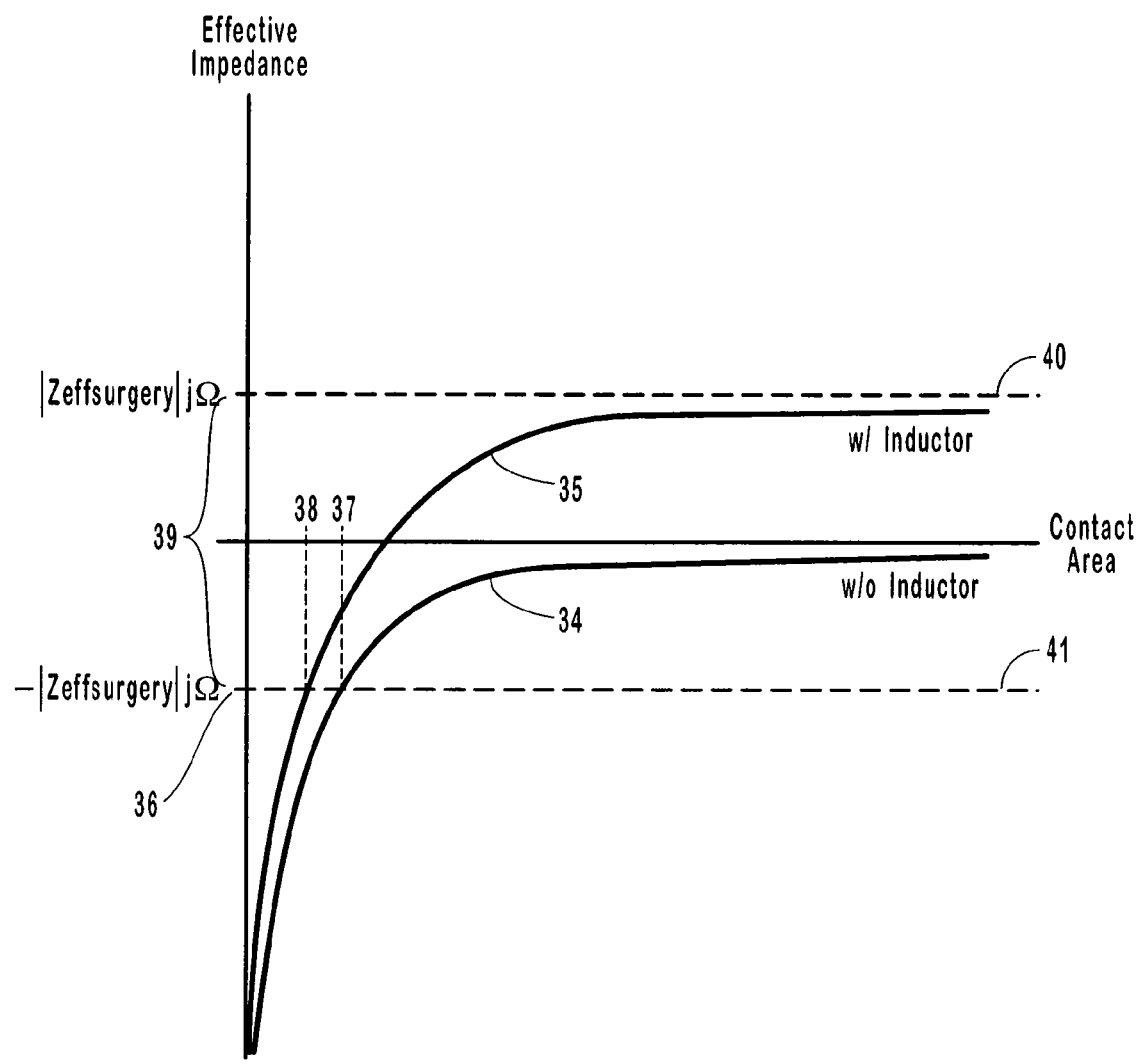
FIG. 5B is a chart illustrating in graphical form the relationship between the effective impedance of a return electrode, the contact area between a patient and a return electrode, and the effect of an inductor on the effective impedance.
Figure 5C:
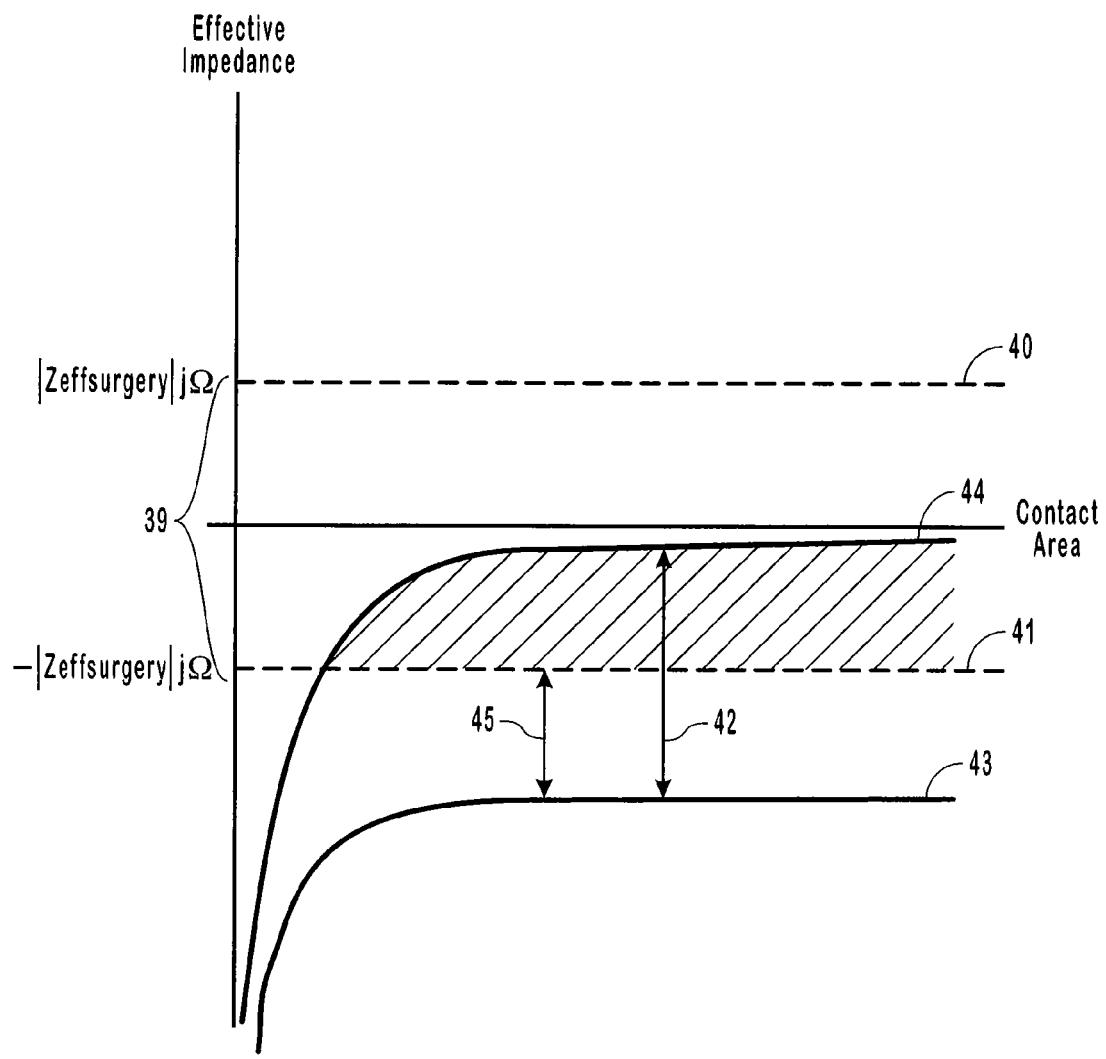
Figure 5D:
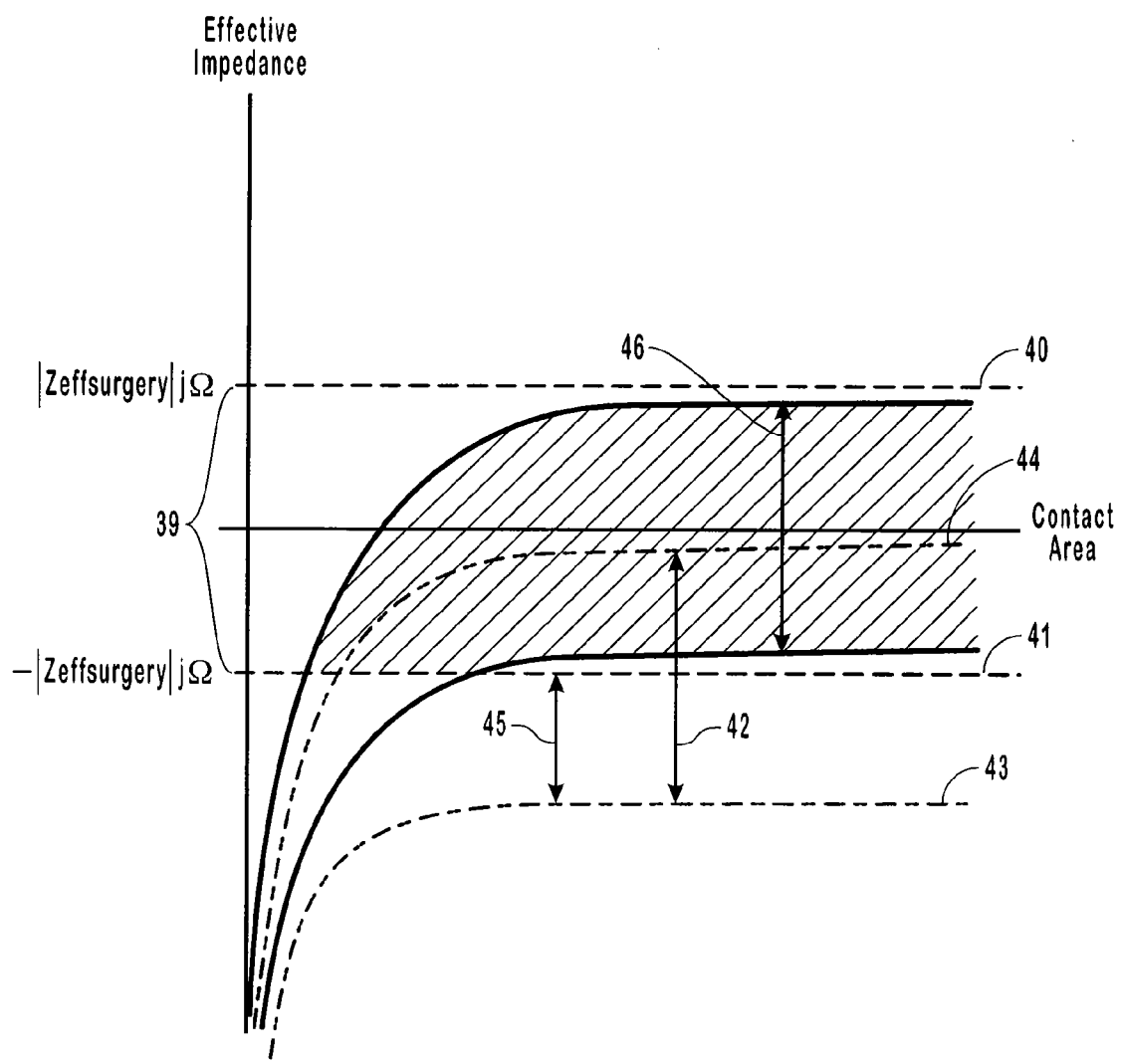

With reference now to FIG. 5B, there is shown a chart illustrating in graphical form the relationship between the effective impedance of a return electrode, the contact area between a patient and a return electrode, and the influence of an inductor on the effective impedance. However, before proceeding to a consideration of such chart, it should be noted that the chart is simplified so as to illustrate the principles underlying the invention and does not represent actual data that may vary substantially. The line graphs illustrate the effective impedance of a return electrode as a function of contact area between the patient and the return electrode. The upper line graph represents the effective impedance of a return electrode where no inductor is coupled in series with the return electrode. The lower line graph represents the effective impedance of a return electrode where an inductor is coupled in series with the return electrode.

The effective impedance of the return electrode is inversely proportional to the contact area A. Where the patient contact area is less than the minimum contact area ($A_{contact(min)}$) the effective impedance of the return electrode increases sharply. However, where the patient contact area is greater than the $A_{contact(min)}$ there is minimal change in the effective impedance of the return electrode. The minimal change in the effective impedance of the return electrode when the contact area is greater than $A_{contact(min)}$ allows a inductor having a set amount of inductance to minimize most of the capacitive reactance of the return electrode. However, the sharp increase in the effective impedance of the return electrode when the contact area is less than $A_{contact(min)}$ limits the ability of the inductor to minimize the capacitive reactance of the return electrode. Where the amount of contact area between the patient and the return electrode is sufficient to conduct effective electrosurgery, the inductor coupled in series with the return electrode counteracts the effective bulk impedance of the electrosurgical return electrode. Where the amount of contact area between the patient and the return electrode is insufficient to conduct safe electrosurgery, the self-limiting aspects of the return electrode is maintained and the electrosurgical current is limited to safe levels. In other words, the inductive reactance provided by the inductor is selected to be insufficient to minimize the capacitive reactance of the return electrode when the capacitive reactance is greater than a threshold level. The capacitive reactance is greater than the threshold level when the contact area between the patient and the return electrode is not safe with respect to current densities.

Variable Inductor

Figure 6:
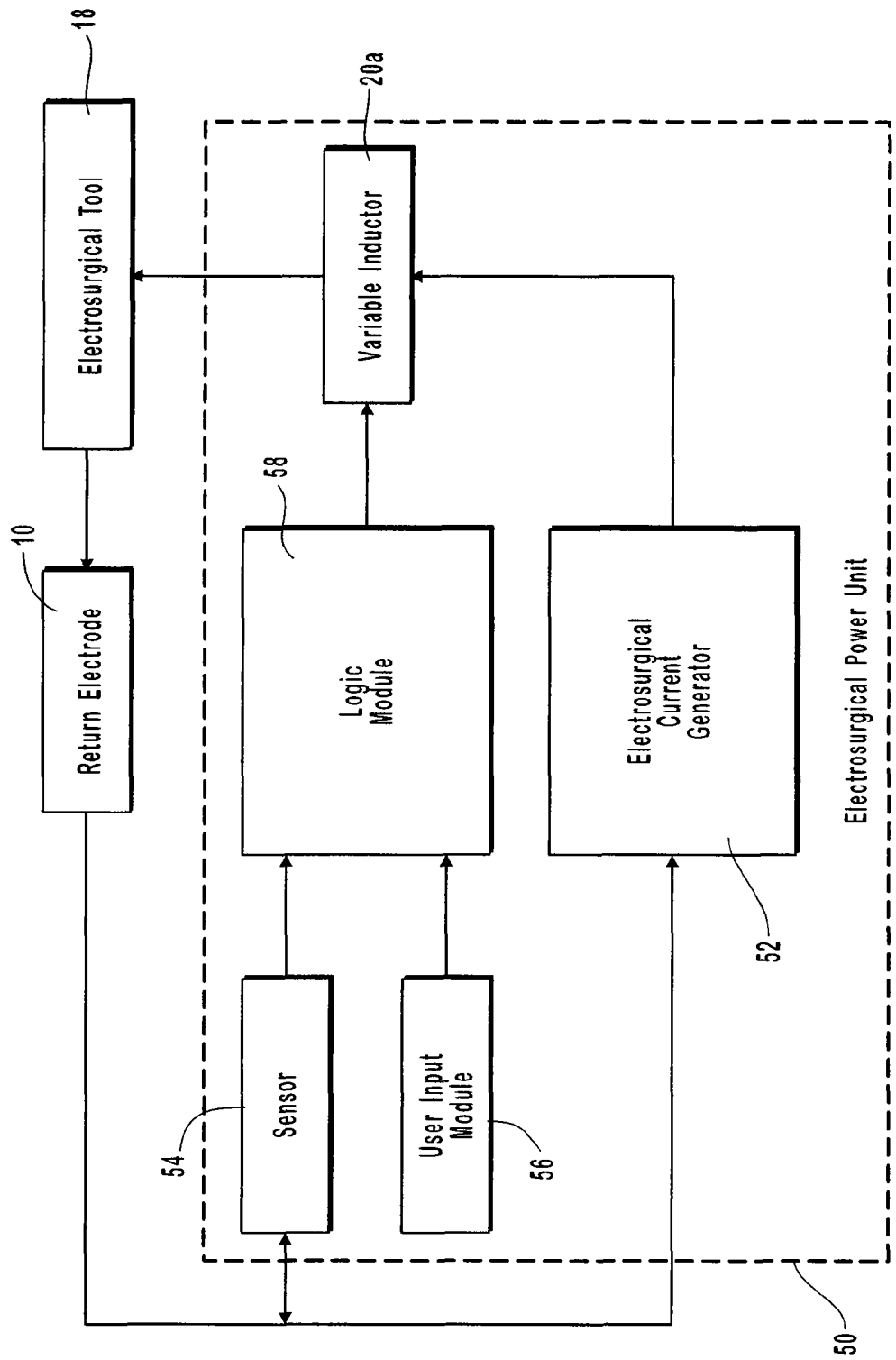
FIG. 6 is a block diagram illustrating an electrosurgical power unit having a tunable variable inductor.

With reference now to FIG. 6, there is shown a variable inductor 20a connected in series with a return electrode 10. There is also shown an electrosurgical power unit 50 having a logic module 58 adapted to tune variable inductor 20a to optimize the flow of the electrosurgical current by minimizing the capacitive reactance in the electrosurgical pathway. In the illustrated embodiment, electrosurgical power unit 50 comprises an electrosurgical generator 52, a sensor 54, a user input module 56, and a logic module 58. Variable inductor 20a is positioned internal to electrosurgical power unit 50. There is also shown an electrosurgical tool 18 and a return electrode 10 connected in series with the variable inductor 20a. The apparatus of FIG. 6 is but one example of a mechanism for controlling the variable inductor. As will be appreciated by those skilled in the art, a variety of types and configurations of mechanisms can be utilized to control the variable inductor without departing from the scope and spirit of the present invention.

Variable inductor 20a is configured to provide different amounts of inductance in the electrosurgical pathway. This allows the amount of inductive reactance to be varied as the capacitive reactance varies. As discussed with reference to FIGS. 5A and 5B, the capacitive reactance varies as a function of the contact area and the materials between the patient and the return electrode 10. Due to the manner in which self-limiting return electrodes are typically used, the contact area and the amount of capacitive reactance in the electrosurgical pathway will often fluctuate. By utilizing variable inductor 20a, the amount of inductance can be changed corresponding with changes in the capacitive reactance to provide optimal levels of electrosurgical current flow. In the preferred embodiment, the amount of inductance that can be provided by the variable inductor is limited such that the capacitive reactance can only be minimized when the contact area between the patient and the return electrode is greater than the minimum contact area. This allows the variable inductor to counteract the capacitive reactance of the return electrode when the patient is in sufficient contact area with the electrosurgical electrode to perform safe and effective electrosurgery. However, when the contact area is less than the minimum contact area, the effective impedance of the pad is sufficient to limit the electrosurgical current to safe levels.

As will be appreciated by those skilled in the art, a variety of types and configurations of variable inductors can be utilized to provide varying amounts of inductance in the electrosurgical pathway. For example, in one embodiment, the variable inductor 20 comprises a plurality of inductors that are configured to be utilized alone, or in combination, to provide varying amounts of inductance in the electrosurgical pathway, with each inductor providing a set amount of inductance. In an alternative embodiment, the variable inductor comprises an electromechanical inductor that is regulated by a control module to provide varying amounts of inductance.

Sensor 54 and logic module 58 are adapted to determine the amount of capacitive reactance in the electrosurgical pathway and tune the variable inductor to optimize the flow of the electrosurgical current by minimizing the capacitive reactance. Sensor 54 is configured to identify the properties of the electrosurgical current returning to the electrosurgical power unit 50 from return electrode 10. Sensor 54 then relays the information regarding the properties of the electrosurgical current to logic module 58. Logic module 58 utilizes the properties of the electrosurgical current to determine the amount of impedance in the electrosurgical pathway and calculate the amount of capacitive reactance in the electrosurgical pathway. Once the amount of impedance in the electrosurgical pathway is determined, the logic module tunes the variable inductor 20 to provide a desired amount of inductive reactance to minimize the capacitive reactance in the electrosurgical pathway. A variety of types and configurations of sensors and logic modules can be utilized within the scope and spirit of the present invention. For example, in one embodiment, the sensor and the logic module are integrated in a microprocessor. In an alternative embodiment, the sensor and logic module comprise separate hardware circuitry.

User input module 56 is configured to allow a user to provide input to logic module 58 to control the amount of inductance provided by variable inductor 20. The functionality, configuration, and purpose of user input module can be tailored to the needs of the user. For example, the user input module can include a button allowing the user to place the electrosurgical power unit in a condition preferred for specialize procedures such as neonatal surgeries or TURP procedures. When the electrosurgical power unit is in a condition preferred for specialize procedures, logic module 58 a tunes variable inductor 20 to minimize the impedance to the extent required, or based on special properties of the electrosurgical apparatus employed, for those procedures.

Figure 7:
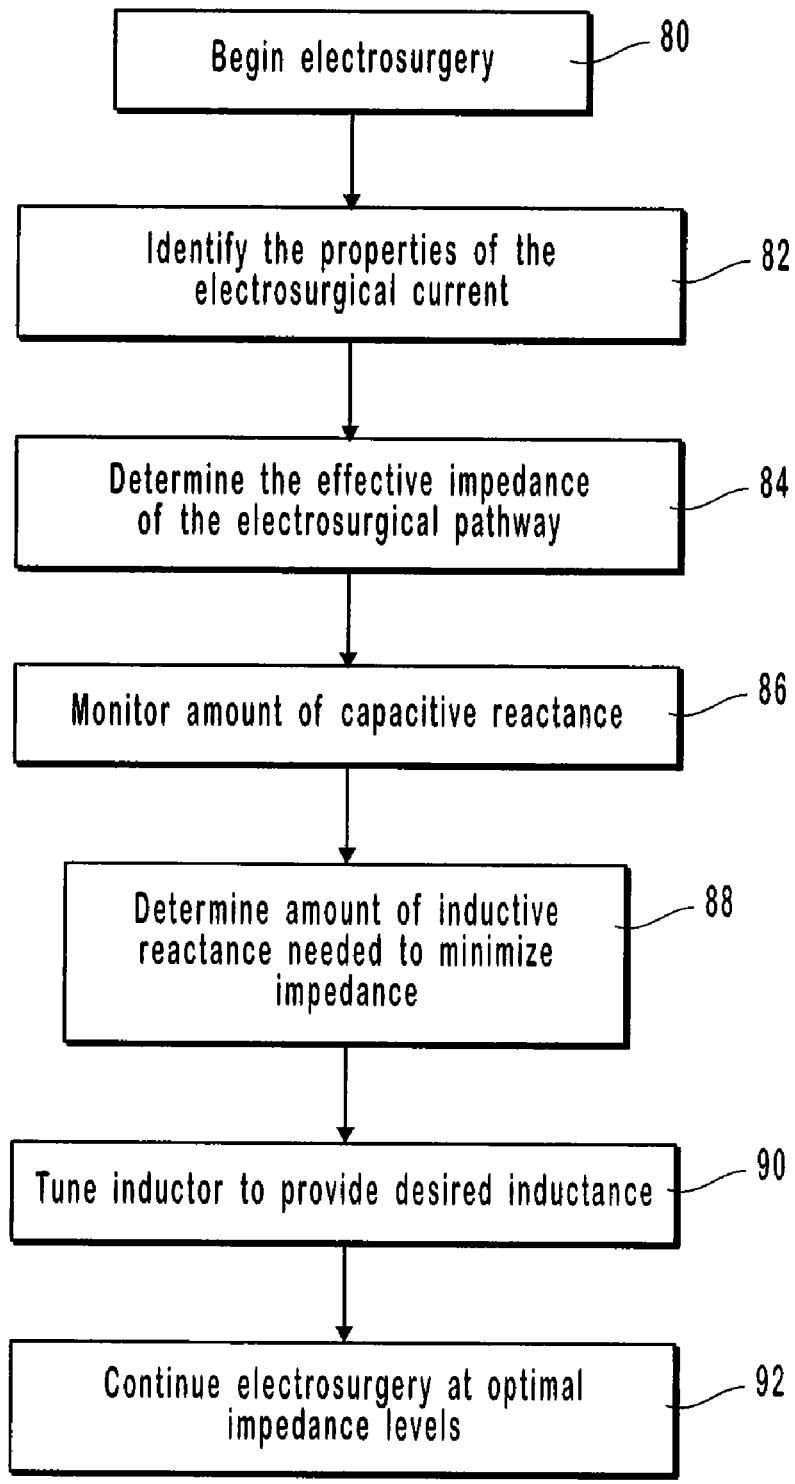
FIG. 7 is a flow diagram illustrating a method for utilizing a variable inductor to change the amount of inductance based on the amount of contact area between the patient and the electrosurgical return electrode.

With reference now to FIG. 7, there is shown a method for utilizing a variable inductor to provide an amount of impedance based on a patient contact area. According to the method, electrosurgery is started in step 80. Once electrosurgery is started, the properties of the electrosurgical current are identified in step 82. Based on the properties of the electrosurgical current, the effective impedance exhibited by the electrosurgical pathway is determined in step 82. Based on the effective impedance exhibited by the electrosurgical pathway, the amount of capacitive reactance of the return electrode is calculated in step 86. Using the amount of capacitive reactance of the return electrode, the amount of inductive reactance needed to minimize the impedance of the return electrode is determined in step 88. The variable inductor is then tuned to provide the amount of inductance necessary to realize the needed inductive reactance in step 90. Once the variable inductor is tuned to provide the desired amount of inductance, electrosurgery is continued at optimal impedance levels in step 92.

A variety of methods for identifying a capacitive reactance and tuning a variable inductor can be utilized without departing from the scope or spirit of the present invention. For example, an electrode of the size and type that is typically utilized during electrocardiogram procedures can be utilized with a separate monitoring current to determine the capacitive reactance of the return electrode before, during, or after the procedure. In another embodiment, the variable inductor can be continually adjusted during the course of a surgical procedure to provide an optimal amount of inductance as the patient contact area and capacitive reactance varies.

While the present invention is described above primarily with reference to a series inductor for use with a capacitive electrosurgical return electrode, a series capacitor can be utilized with a self-limiting electrosurgical return electrode having an inductive component without departing from the scope and spirit of the present invention. In the embodiment, the series capacitor provides a level of capacitive reactance needed to counteract the inductive reactance of the electrosurgical return electrode. A variety of type and configuration of the series capacitors can be utilized without departing from the scope and spirit of the present invention.

Contact Quality Monitoring

Figure 8:
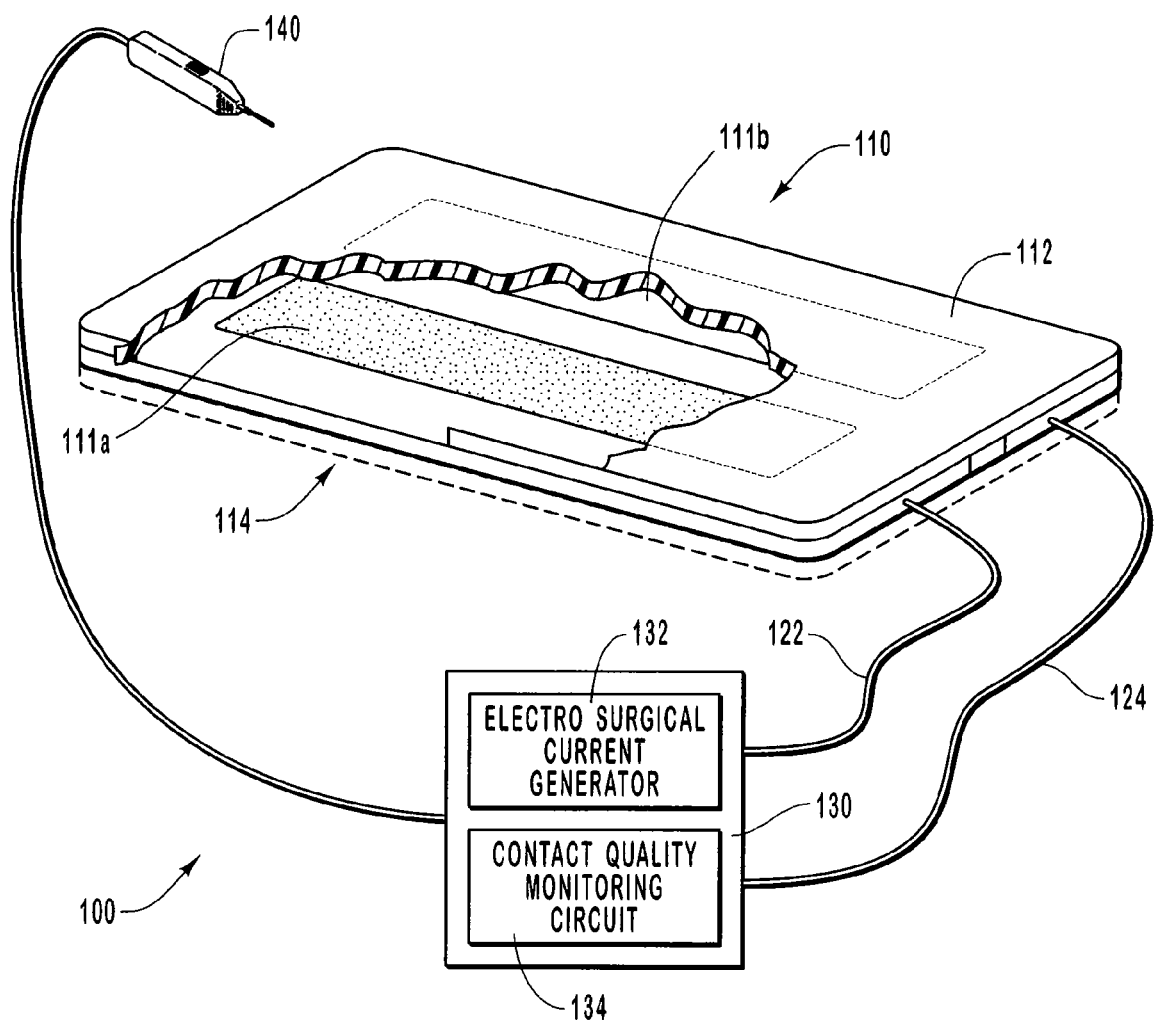
FIG. 8 is a perspective view of an electrosurgical return electrode for use with a contact quality monitoring apparatus having a semi-insulating member and conductor members according to the present invention.

With reference now to FIG. 8, there is shown an electrosurgical system 110 that utilizes one or more aspects of the present invention. As depicted, system 100 includes an electrosurgical return electrode 110 that communicates with an electrosurgical power unit 130 via members 122 and 124. The electrosurgical power unit 130 delivers electrosurgical signals or radio frequency (RF) energy to an electrosurgical tool or instrument 140 that can be used during a procedure to cut and/or coagulate tissue of a patient.

The electrosurgical power unit 130 also includes contact quality monitoring circuitry 134. In the illustrated embodiment, circuitry 134 creates a contact quality monitoring signal that is delivered to electrosurgical return electrode 110 utilizing member 124. In other configurations, the monitoring signal is deliverable along members 122 and/or 124. This monitoring signal can have a variety of different waveforms, frequencies, power levels, phase angle, or combinations thereof to allow circuitry 134 to measure, sense, and/or track the monitoring signal as it is delivered to and received from electrosurgical return electrode 110 along the monitoring path; the path extending from electrosurgical power unit 130, along member 124, through electrosurgical electrode 110 and a patient (not shown), and returning to electrosurgical power unit 130 along member 122. Differences in power, waveform, frequency, phase angle, or any other measurable characteristic or property of the monitoring signal can be measured, sensed, and/or tracked to identify whether a patient (not shown) is sufficiently in contact with electrosurgical electrode 110 to prevent patent burns.

In addition to the above, it will be appreciated by those skilled in the art that the monitoring signal and associated circuitry and path can be configured to provide a variety of information relating to the contact area between the patient and a return electrode of a variety of types and complexities. For example in one embodiment of the present invention, the monitoring circuitry can be configured to simply determine when the contact area falls below a predetermined threshold. In an alternative embodiment, the monitoring circuitry can be configured to determine the actual contact area and provide related information such as the amount of electrosurgical current and/or current densities. In yet another embodiment, the monitoring circuitry provides information needed to tune a variable inductor so as to counteract capacitive reactance in the electrosurgical circuit.

As shown, electrosurgical return electrode 110 electrically communicates with electrosurgical power unit 130 through members 122 and 124. Return electrode 110 is adapted to prevent patient burns by providing self-limiting capabilities and to cooperate with circuitry 134 to determine whether the contact area between the patient and return electrode 110 is below a given threshold.

Return electrode 110, in the exemplary embodiment, includes a semi-insulating member 112 and a conductor member 114. In this configuration, semi-insulating member 112 is adapted to provide the self-limiting characteristics or capabilities of return electrode 110. Conductor member 114 is configured to permit contact quality monitoring circuitry to determine the contact area between return electrode 110, such as but not limited to semi-insulating member 112, and a patient resting thereon. In the illustrated embodiment, conductor member 114 has a split-plate configuration with a first conductor 111a and a second conductor 111b. Conductor member 114 need not be in direct physical contact with the patient. A patient can be in electrical connection with first conductor 111a and second conductor 111b without requiring the use of adhesives or gels. This also allows return electrode 110 to be re-used thereby eliminating the need and cost of disposable split-plate electrodes that are currently used.

In the illustrated embodiment, a monitoring signal is passed to conductor member 114, i.e. from first conductor 111a to second conductor 111b. Members 122 and 124 operate to relay the monitoring signal to and from contact quality monitoring circuit 134. At least one of members 122 and 124 also operates as the return path of the electrosurgical current. Where the contact area between the patient and return electrode 110 is very low, the total effective impedance on the monitoring signal or current will be very high and the amount of monitoring signal or current will be minimized. Where the contact area between the patient and electrode 110 is above the minimum contact area, the total effective impedance will be much lower allowing greater monitoring signal or current to flow.

By determining the amount of monitoring signal or current, the contact quality monitoring circuitry 134 determines whether the contact area between the patient and electrode 110, such as but not limited to semi-insulating member 112, is above a predetermined threshold (e.g. minimum contact area). Where the contact area is below the predetermined threshold the monitoring circuitry 134 activates an output device, such as but not limited to, an output device capable of delivering an audible signal, a visual signal, a tactile signal, or a combination thereof, to notify a physician or user that the contact area is insufficient to conduct effective surgery. As will be appreciated by those skilled in the art, the contact quality monitoring circuitry can be configured to determine the amount of contact area between a patient and a return electrode in a variety of manners utilizing an electrosurgical return electrode having one or a combination of a resistive component, a capacitive component, and/or an inductive component.

With reference now to FIG. 9-13 there is shown a variety of configurations of a conducting member for use with circuitry 134 (FIG. 8) of electrosurgical power unit 130, in which the conducting member allows circuitry 134 to determine whether the total contact area between the patient and the return electrode is within a given range or above a threshold level below which the patient receives a burn. One benefit of the configuration of the conducting members of FIGS. 9-13 is that they permit circuitry 134 to optionally determine the amount of contact area between the patient and the return electrode notwithstanding the total surface area of the semi-insulating member and the portion of semi-insulating member the patient is contacting. For the sake of simplicity, the conducting members will be described for use with contact quality monitoring circuitry, however as will be appreciated by those skilled in the art a variety of types and configurations of circuitry can be utilized within the scope and spirit of the present invention to determine whether the contact area between the patient and the semi-insulating member is below a given threshold.

The configuration of the conducting members of FIGS. 9-13 is particularly well suited for use with the semi-insulating member 112 of FIG. 8. Semi-insulating member 112 is configured to have a sufficient surface area to permit a patient to contact various portions of semi-insulating member 112 while maintaining a minimum contact area. Traditional split-plate electrodes having two independent conductive layers positioned side-by-side are not configured to allow contact quality monitoring circuitry to determine the amount of contact area independent of the location of the patient on a return electrode. For example, traditional split-plate electrodes are unable to identify that the patient contact area is sufficient to conduct safe and effective electrosurgery where the patient is contacting only one side of the return electrode. The configurations of conductive members of FIGS. 9-13 allow contact quality monitoring circuitry 134 to determine the amount of contact area between the patient and a return electrode notwithstanding the total surface area of the electrode and the portion of the electrode the patient is contacting. While the conducting members of FIGS. 9-13 are particularly well adapted for use with the semi-insulating member 112 of FIG. 8, it will be understood that conducting members of FIGS. 9-13 can be utilized with contact quality monitoring circuitry independently of a semi-insulating member.

Figure 9:
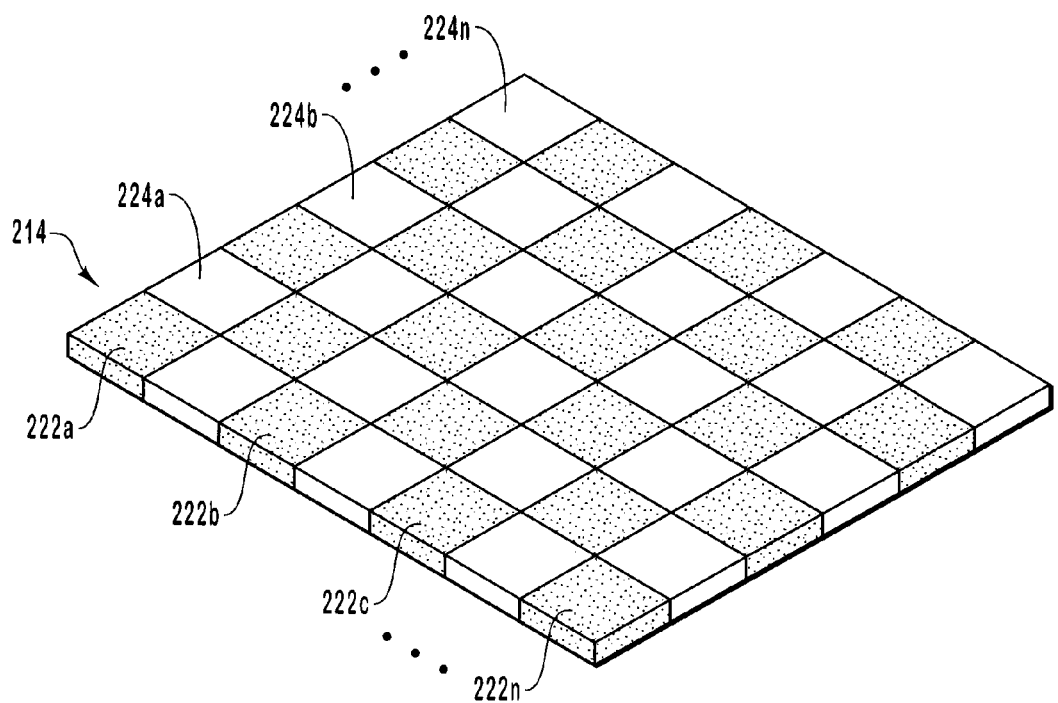
FIG. 9 illustrates a conductor member having a first and second conductor arranged in matrix of alternating segments.

With reference now to FIG. 9, there is shown a conductor member 214 in which segments of a first conductor 222 and a second conductor 224 are arranged in a matrix. First conductor 222 includes segments 222a-222n, while second conductor 224 includes segments 224a-224n. Segments 222a-222n are electrically isolated from segments 224a-224n such that a monitoring signal passes from first conductor 222 to second conductor 224 through the patient rather than directly from segments of first conductor 222 to the segments of second conductor 224.

Segments 222a-222n of first conductor 222 are electrically coupled in parallel. Segments 224a-224n of second conductor 224 are also electrically coupled in parallel. Because the segments are electrically coupled in parallel, the impedance level varies based upon the number of adjacent segments in contact with the patient. The matrix configuration of segments 222a-222n and 224a-224n permits contact quality monitoring circuitry to determine whether the contact area between the patient and the return electrode is sufficient to prevent patient burns or allow effective surgery notwithstanding the total surface area of the semi-insulating member and the portion of semi-insulating member the patient is contacting.

While segments of first conductor 222 and second conductor 224 are depicted as having a checkerboard configuration, it will be understood that a variety of configurations of conductor member 214 are possible. For example, first conductor 222 and second conductor 224 can be arranged in alternating stripes, triangles, ellipses, or any other configuration allowing the contact quality monitoring circuitry to determine the amount of contact area between the patient and the return electrode notwithstanding the total surface area of the return electrode and/or semi-insulating member and the portion of the return electrode and/or semi-insulating member the patient is contacting.

Figure 10:
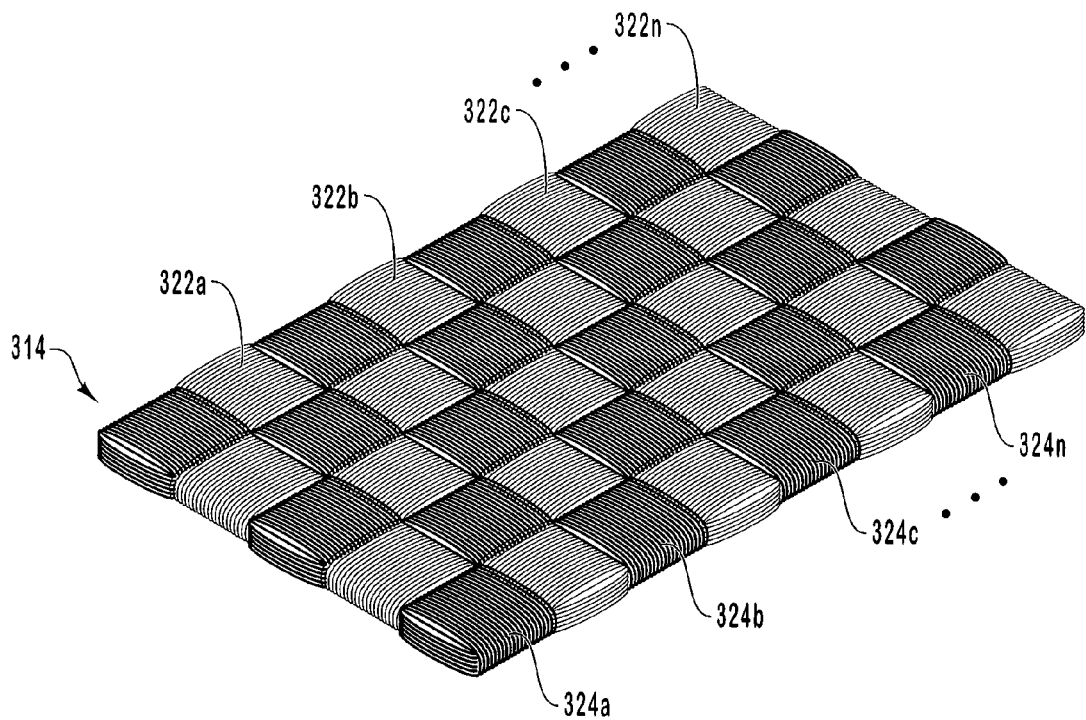
FIG. 10 illustrates a conductor member having a first conductor and a second conductor interwoven in a lattice structure.

FIG. 10 illustrates another alternate configuration of a conductor member 314. As illustrated, conductor member 314 includes a first conductor 322 and second conductor 324 that are interwoven in a lattice structure. The segments 322a-322n and 324a-324n are electrically coupled in parallel. Additionally, first and second conductors 322 and 324, respectively, are electrically isolated from one another. The interwoven lattice structure permits the segments to alternate while providing a configuration that allows for efficient and convenient manufacture of conductor 314.

Figure 11A:
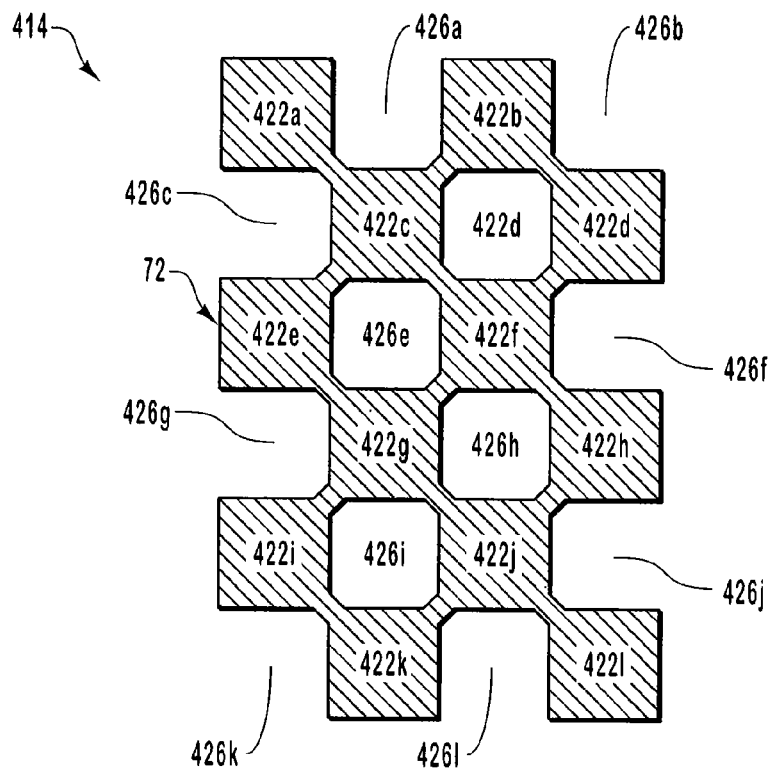
FIG. 11A,B illustrate a first conductor and a second conductor that are configured to comprise a conductor member.
Figure 11B:
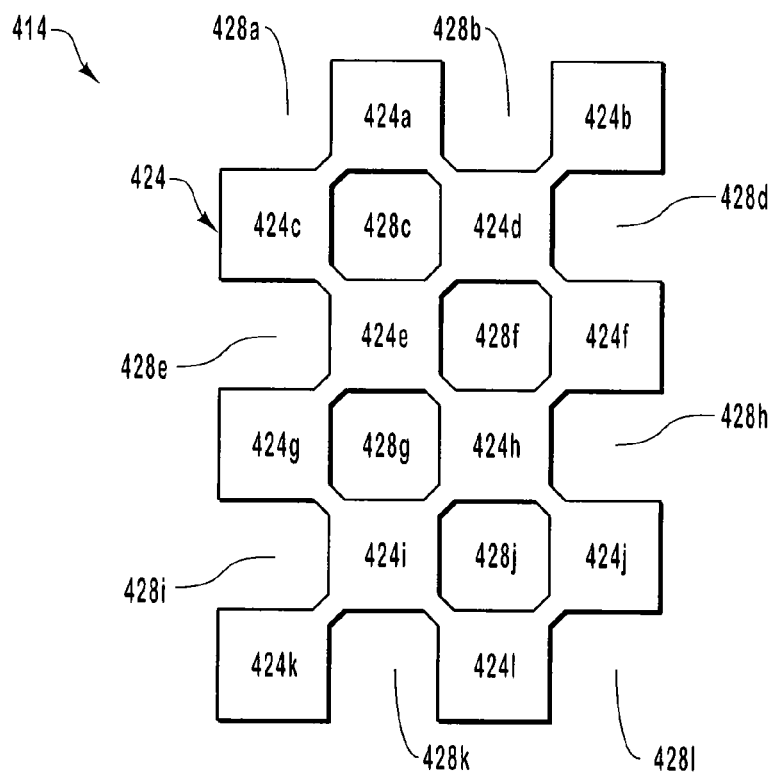

FIGS. 11A and 11B illustrate a first conductor 422 and second conductor 424 that are configured to form conductor member 414 having a split-plate type configuration. In the illustrated embodiment first conductor 422 includes a plurality of segments 422a-422n. Segments 422a-422n are defined by a plurality of voids 426a-426n. Similarly, second conductor 424 includes a plurality of segments 424a-424n and a plurality of voids 428a-428n. First conductor 422 and second conductor 424 can be manufactured by stamping a sheet of conductive material to create the segments and voids, or by any other acceptable manufacturing process. The segments and voids of first conductor 422 are configured to be out of alignment with the segments and voids of second conductor 424 such that when the first conductor 422 is placed over the second conductor 424 a matrix analogous to that shown in FIG. 9 is created.

As will be appreciated by those skilled in the art, the configuration of the conductor member is not limited to that shown in FIGS. 9-11. A variety of configurations of a conductor member can be utilized which allow the conductor member to be utilized with contact quality monitoring circuitry to determine the amount of contact area between the patient and the return electrode notwithstanding the total surface area of the semi-insulating member and the portion of the electrode and/or the semi-insulating member the patient is contacting. For example, a first conductor having a plurality of apertures formed therethrough can be placed in electrical isolation over a second continuous sheet conductor such that when a patient is positioned over a portion of the return electrode a monitoring signal can pass from the first conductor to the second conductor through the apertures.

Figure 12:
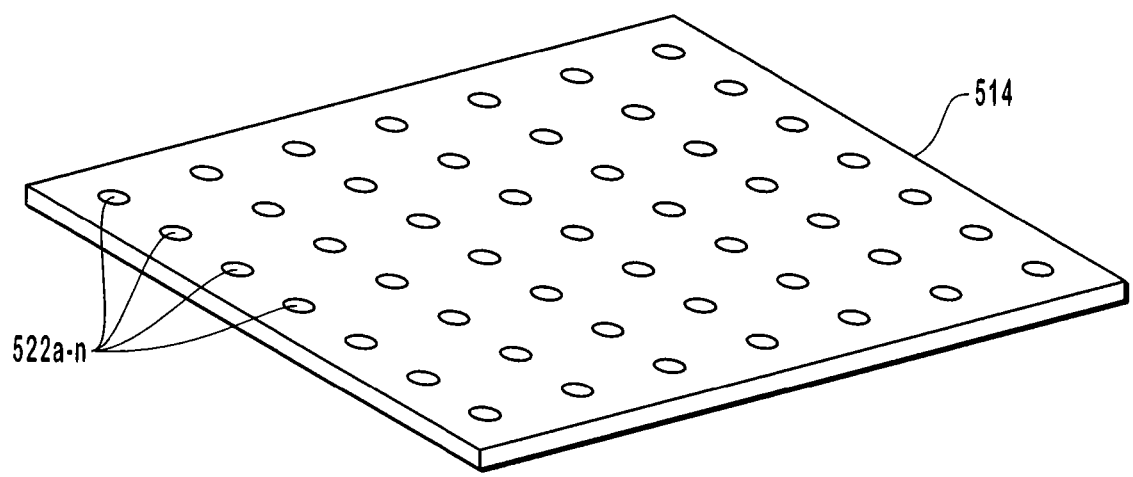
FIG. 12 is a perspective view illustrating a conductor member having a plurality of membrane switches.

With reference now to FIG. 12, there is shown a conductor member 514 having a plurality of membrane switches 522a-522n. The membrane switches electronically communicate with contact quality monitoring circuitry to receive a monitoring signal and return all or a portion of the signal to circuitry. In the illustrated embodiment, the plurality of membrane switches 522a-522n are adapted to permit circuitry to determine whether the contact area between the patient and return electrode is below a given threshold or threshold level below which the patient receives a burn. The configuration of membrane switches 522a-522n allows the contact area to be determined notwithstanding the total surface area of the return electrode and the portion of the return electrode the patient is touching. A variety of mechanisms can be utilized to determine the number of membrane switches depressed including, but not limited to, software, digital circuits, and the like.

As will be appreciated by those skilled in the art, while conductor member 514 is depicted as having a plurality of membrane switches 522a-522n, a variety of mechanisms can be used in the place of membrane switches without departing from the scope and spirit of the present invention. For example, an alternative electrical, mechanical, electromechanical, and/or any other mechanism can be used with conductor member 514 to indicate the amount contact area between the patient the return electrode such that a contact quality monitoring circuit can determine the amount of contact area between the patient and the return electrode notwithstanding the total surface area of the semi-insulating member and the portion of semi-insulating member the patient is contacting.

Figure 13:
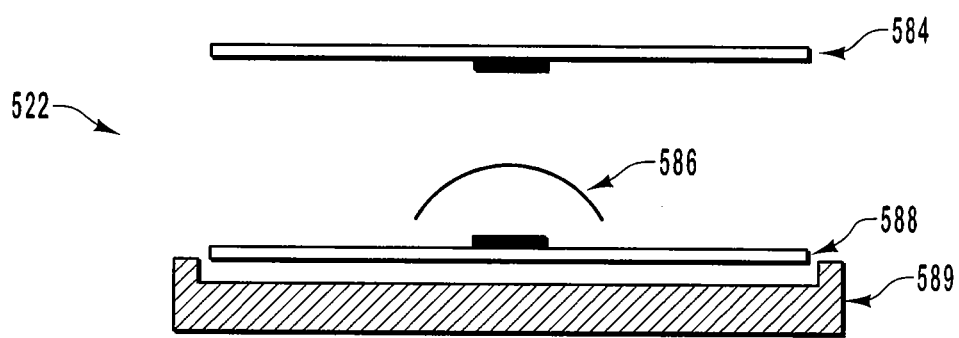
FIG. 13 is a cross-sectional exploded view illustrating the components of a membrane switch that can be utilized in connection with the conductor member of FIG. 12.

FIG. 13 illustrates exemplary components of a membrane switch 522 that can be utilized in connection with the conductor member 514 of FIG. 12. In the illustrated embodiment, membrane switch 522 includes a membrane layer 584, a tactile layer 586, a static layer 588, and a rigid layer 589. The membrane layer 584 includes a first conductor adapted to receive a monitoring signal or current from contact quality monitoring circuitry and is configured to be deformed in response to a force acting thereon. The tactile layer 586 includes a dome member and is configured to separate the membrane layer 584 from electrically coupling to static layer 588 until a force is applied to tactile layer 586 to deform tactile layer 586 so that tactile layer 586 comes into contact with static layer 588.

Static layer 588 comprises a second conductor configured to receive the monitoring signal or current from membrane layer 584 when membrane layer 584 and the tactile layer 586 are deformed. The static layer 588 is electrically coupled to contact quality monitoring circuitry to complete the monitoring path and allow circuitry 134 (FIG. 2) to determine the contact area between the patient and the return electrode.

The rigid layer 589 is configured to provide a substrate to prevent deformation of static layer 588 and maintain electrical coupling between membrane layer 584 and the static layer 588 when tactile layer 586 is deformed. In the illustrative embodiment, membrane layer 584 of each membrane switch is electrically coupled in parallel with the membrane layers of all the other membrane switches while the static layer 588 of each membrane switch is electrically coupled in parallel with the membrane layers of all other membrane switches.

As will be appreciated by those skilled in the art, a variety of types and configurations of membrane switches can be utilized without departing from the scope or spirit of the present invention. For example, in one embodiment a single static layer comprising a first conductor is positioned to be in contact with a plurality of membrane layers comprising a plurality of second conductors such that when a user is in contact with the surgical surface of the return electrode a monitoring signal can pass between the first conductor and each of the second conductors positioned in the portion of the return electrode in contact with the patient. The properties of the monitoring signal vary with the number of second elements passing a monitoring signal to the first element. The properties of the monitoring signal represent the amount of contact area between the patient and the electrosurgical surface.

Although the invention hereof has been described by way of preferred embodiments, it will be evident that adaptations and modifications may be employed without departing from the spirit and scope thereof.

The terms and expressions employed herein have been used as terms of description and not of limitation; and, thus, there is no intent of excluding equivalents, but, on the contrary, it is intended to cover any and all equivalents that may be employed without departing from the spirit and scope of the invention.

What is claimed is:

1. A self-limiting electrosurgical return electrode comprising:
   a semi-insulating member for limiting the density of electrosurgical current flowing through the electrode to less than a predetermined level to prevent a patient burn; and
   a conductor member coupled to the semi-insulating member, the conductor member having a split plate configuration and coupled to circuitry for monitoring the contact area between the electrode and a patient, wherein the circuitry is configured to measure at least one of an electrosurgical current or electrosurgical current density flowing through the electrode.

2. The self-limiting electrosurgical return electrode of claim 1, wherein the conductor member comprises a first conductor electrically isolated from a second conductor.

3. The self-limiting electrosurgical return electrode of claim 1, wherein the first conductor and a second conductor interwoven in a lattice structure 4. The self-limiting electrosurgical return electrode of claim 3, wherein the circuitry measures the impedance between the first conductor and the second conductor.

5. The self-limiting electrosurgical return electrode of claim 1, wherein the conductor member comprises a plurality of membrane switches.

6. The self-limiting electrosurgical return electrode of claim 1, wherein the electrode further comprises one or a combination of a resistive component, a capacitive component, and an inductive component.

7. A self-limiting electrosurgical return electrode comprising:

a semi-insulating member having a working surface adapted for disposition adjacent the tissue of a patient positioned thereon for electrosurgery and that continuously and automatically regulates the electrosurgical current flowing through the electrode as a function of the area of contact between the electrode and the patient's tissue so as to limit the density of electrosurgical current to less than 100 milliamperes per square centimeter of the electrode; and a conductor member coupled to the semi-insulating member, having a split plate configuration, and coupled to circuitry in electrical communication with the electrically conducting member, the conductor member and the circuitry configured to determine the contact area between the electrode and the patient.

8. The self-limiting electrosurgical return electrode of claim 7, wherein the semi-insulating member comprises a silicone rubber material impregnated with conductive fibers.

9. The self-limiting electrosurgical return electrode of claim 7, further comprising an inductor in electrical series with the semi-insulating member.

10. The self-limiting electrosurgical return electrode of claim 7, further comprising a variable inductor in electrical series with the semi-insulating member to minimize capacitive reactance.

11. The self-limiting electrosurgical return electrode of claim 7, wherein the first conductor and a second conductor arranged in one of alternating geometric shapes to aid with determining the amount of contact area between the patient and the electrode.

12. The self-limiting electrosurgical return electrode of claim 11, wherein the geometric shape comprises strips, triangles, or ellipses.

13. A self-limiting electrosurgical system comprising:
a self-limiting electrosurgical return electrode comprising:
    a semi-insulating member having a bulk impedance sufficient to prevent a patient burn when a contact area between a patient and the semi-insulating member is below a given threshold; and
    a conductor member coupled to the semi-insulating member, the conductor member having a split plate configuration,
    wherein an effective impedance of the self-limiting electrosurgical return electrode is below 100 ohms; and
    contact quality monitoring circuitry coupleable to the conductor member, the combination of the contact quality monitoring circuitry and the conductor member monitoring the contact area between the semi-insulating member and the patient and activating an output device if the contact area is below a predetermined threshold.

14. The self-limiting electrosurgical system of claim 13, further comprising an electrosurgical generator in electrical communication with the semi-insulating member.

15. The self-limiting electrosurgical system of claim 13, further comprising an inductor in series with the electrosurgical return electrode, the inductor counteracting at least a portion of an effective impedance of the electrosurgical return electrode and a patient.

16. The self-limiting electrosurgical system of claim 15, wherein the inductor is selected such that the effective impedance of the electrosurgical return electrode, the patient, and the inductor falls within a range of impedances at which effective electrosurgery can be performed for a selected group of patients.

17. The self-limiting electrosurgical system of claim 15, wherein said inductor is selected from the group consisting of a solid state inductor, an electro-mechanical inductor, a fixed inductor, a variable inductor, solid state wave shaping circuitry or any combination thereof.

18. The self-limiting electrosurgical system of claim 13, wherein by minimizing the effective impedance to below 100 ohms electrosurgical surgery on patients weighing less that 25 pounds can be performed.

19. The self-limiting electrosurgical system of claim 13, wherein by minimizing the effective impedance to below 100 ohms the electrosurgical return electrode can be utilized for neonatal applications.

20. The self-limiting electrosurgical system of claim 13, wherein the self-limiting electrosurgical return electrode comprises electrically conducting material having an effective bulk impedance equal to or greater than about 4,000 $\Omega\cdot cm$.

21. The electrosurgical apparatus of claim 13, wherein the self-limiting electrosurgical return electrode having an effective bulk impedance equal to or greater than about 10,000 $\Omega\cdot cm$.

* * * * *